United States Patent [19]

Murakami et al.

[11] 4,109,088

[45] Aug. 22, 1978

[54] 2-(INDENYLOXYMETHYL) MORPHOLINE DERIVATIVES

[75] Inventors: Masuo Murakami; Kozo Takahashi, both of Tokyo; Yuji Kawashima, Kiyose; Tadao Kojima, Shiraoka; Kunihiro Niigata, Ageo; Takashi Fujikura, Hachioji; Yoshihisa Nozaki, Tokyo; Shiro Tachikawa, Omiya; Shinji Usuda, Matsudo; Soichi Kagami, Kawaguchi, all of Japan

[73] Assignee: Yamanouchi Pharmaceutical Co., Ltd., Tokyo, Japan

[21] Appl. No.: 772,320

[22] Filed: Feb. 25, 1977

Related U.S. Application Data

[63] Continuation-in-part of Ser. No. 669,884, Mar. 24, 1976, abandoned, which is a continuation-in-part of Ser. No. 646,844, Jan. 5, 1976, abandoned.

[30] Foreign Application Priority Data

Jan. 29, 1975 [JP] Japan .................................. 50-12177
Dec. 25, 1975 [JP] Japan .................................. 50-155647

[51] Int. Cl.[2] .................................. C07D 265/30
[52] U.S. Cl. .................................. 544/174; 424/248.57
[58] Field of Search .................................. 544/174

[56] References Cited

U.S. PATENT DOCUMENTS 3,714,161 1/1973 Mallion et al. ....................... 544/174

*Primary Examiner*—Henry R. Jiles
*Assistant Examiner*—R. W. Ramsuer
*Attorney, Agent, or Firm*—Burgess, Ryan and Wayne

[57] ABSTRACT

2-(Indenyloxymethyl) morpholine derivatives are disclosed. These derivatives are excellent in methamphetamine stereotyped increasing and antireserpine activities which are useful as antidepression agents.

13 Claims, No Drawings

2-(INDENYLOXYMETHYL) MORPHOLINE DERIVATIVES

CROSS-REFERENCE TO RELATED APPLICATIONS

This application is a continuation-in-part of our co-pending U.S. patent application Ser. No. 669,884, filed Mar. 24, 1976, now abandoned which, in turn, is a continuation-in-part of our co-pending U.S. patent application Ser. No. 646,844, filed Jan. 5, 1976, now abandoned.

BACKGROUND OF THE INVENTION

1. Field of the Invention

The present invention relates to novel 2-(indenyloxymethyl)-morpholine derivatives and more particularly it relates to 2-(indenyloxymethyl) morpholine derivatives possessing excellent methamphetamine stereotyped increasing and antireserpine activities which are desirable properties for antidepression agents.

2. Description of the Prior Art

As an antidepression agent having a morpholine ring, there are known the compounds as described in, for example, U.S. Pat. No. 3,714,161 (British Pat. No. 1,138,405; Belgian Pat. No. 708,557; Canadian Pat. No. 860,341; Australian Pat. No. 6,730,109; Swiss Pat. Nos. 504,452 and 513,904; French Pat. No. 1,571,341; French Medical Specific Pat. No. 7557, etc.,) and U.S. Pat. No. 3,712,890 (British Pat. No. 1,260,886; Canadian Pat. No. 913,090; Swiss Pat. No. 539,068; etc.).

The compound which is believed to possess the highest activity among the compounds disclosed in the aforementioned patents is 2-(2-ethoxyphenoxymethyl) morpholine which is generally known as Viloxazine (see Nature, 238, 157–158 (1972)). A series of investigations made by K. B. Mallion, A. H. Todd, R. W. Turner, et al who are the inventors of Viloxazine suggest the relation between the chemical structures and the pharmacological activities thereof. That is, it is preferred that the compound has one substituent at the 2-position of a phenoxy group bonded to morpholine. Furthermore, when the phenoxy group forms a fused ring, it is preferred that, for example, a tetralin-type ring is formed by the condensation of a tetramethylene group. However, when the condensed ring forms an indane-type ring by the condensation of a trimethylene group, the pharmacological effect is diminished.

SUMMARY OF THE INVENTION

As the result of various investigations in discovering excellent antidepression agents, the inventors have discovered that a novel indene-type compound which is similar to an indane-type compound shows an unexpectedly excellent medical effect contrary to the aforesaid suggestion.

That is, according to the present invention, there are provided 2-(indenyloxymethyl) morpholine derivatives represented by the general formula IV:

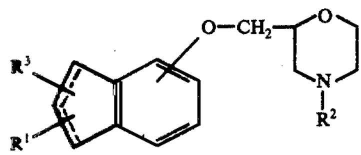

wherein $R^1$ and $R^3$ each represents a hydrogen atom, a lower alkyl group, or a phenyl group, $R^2$ represents a hydrogen atom, a lower alkyl group, a cycloalkyl group, a phenyl group, or a benzyl group, one of the dotted lines means a single bond and the other means a double bond, or the tautomeric mixtures thereof, and the nontoxic pharmaceutically acceptable salts thereof.

The aforementioned compounds of this invention possess excellent methamphetamine stereotyped increasing and antireserpine activities which are desirable properties for an antidepression agent.

DESCRIPTION OF THE PREFERRED EMBODIMENTS

As the lower alkyl groups shown by $R^1$ and $R^2$ of the compounds of this invention represented by the general formula IV, there are straight chain, branched chain, and cyclic alkyl groups having up to 6 carbon atoms. Typical examples of the straight chain or branched chain alkyl groups are a methyl group, an ethyl group, a propyl group, an isopropyl group, a butyl group, an isobutyl group, a pentyl group, a neopentyl group, a hexyl group, an isohexyl group, etc., and examples of the cyclic alkyl groups are a cyclopentyl group, a cyclohexyl group, etc.

Typical examples of the compound of this invention are 2-(7-indenyloxymethyl)-4-isopropylmorpholine, 4-butyl-2-(7-indenyloxymethyl)morpholine, 2-(7-indenyloxymethyl)-4-methylmorpholine, 4-ethyl-2-(7-indenyloxymethyl)morpholine, 2-(7-indenyloxymethyl)-morpholine, 2-(7-indenyloxymethyl)-4-propylmorpholine, 4-cyclohexyl-2-(7-indenyloxymethyl)morpholine, 4-benzyl-2-(7-indenyloxymethyl)-morpholine, 2-(7-indenyloxymethyl)-4-phenylmorpholine, 2-(4-indenyloxymethyl)morpholine, 2-(3-methyl-7-indenyloxymethyl)-morpholine, 4-isopropyl-2-(3-methyl-7-indenyloxymethyl)morpholine, 4-isopropyl-2-(3-methyl-4-indenyloxymethyl)morpholine, 4-isopropyl-2-(3-methyl-5-indenyloxymethyl)morpholine, 4-isopropyl-2-(1-methyl-3-phenyl-6-indenyloxymethyl)morpholine, 2-(5-indenyloxymethyl)-4-isopropyl-morpholine, 2-(6-indenyloxymethyl)-4-isopropylmorpholine, 4-isopropyl-2-(3-phenyl-6-indenyloxymethyl)morpholine, etc.

The morpholine derivatives of this invention may be used as such or the suitable acid addition salts thereof, i.e., the salts of pharmacologically nontoxic or useful acids. Examples of these acids are inorganic acids such as hydrochloric acid, sulfuric acid, hydrobromic acid, phosphoric acid, etc., and organic acids such as acetic acid, citric acid, malic acid, fumaric acid, maleic acid, oxalic acid, glutamic acid, ascorbic acid, etc.

The subject compounds of this invention are prepared by various methods. For example, the 1-(indenyloxymethyl)-3-amino-2-propanol derivative shown by general formula I:

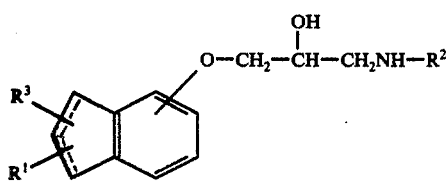

wherein $R_1$, $R^2$, and $R^3$ have the same meanings as in general formula IV is reacted with the haloacetyl halide shown by the formula:

Y—COCH$_2$—X wherein X and Y each represents a halogen atom to form the acyl derivative represented by general formula II:

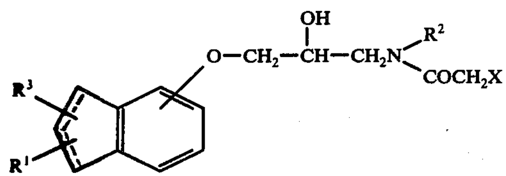

wherein $R^1$, $R^2$, $R^3$ and X have the same meaning as above. The acyl derivative is subjected to a ring closure reaction in the presence of a dehydrohalogenating agent to form the compound shown by general formula III:

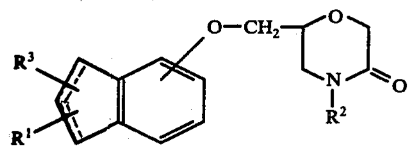

wherein $R^1$, $R^2$, and $R^3$ have the same meaning as above, and then the compound thus obtained is converted into the subject compound of formula IV using a metal hydride complex.

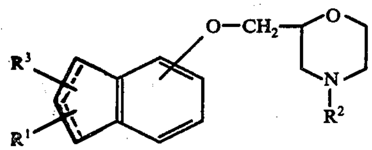

When $R^2$ in the compound of formula IV thus prepared is a benzyl group, the group can be converted into a hydrogen atom by catalytic hydrogenation of the benzyl group in the presence of a palladium-carbon catalyst.

Examples of the haloacetyl halide used in the first stage of the aforesaid reaction are monochloroacetyl chloride, monobromoacetyl bromide, monobromoacetyl chloride, etc. The reaction in the first stage is performed by reacting the starting compound of general formula I with an equimolar or slightly excessive amount of the haloacetyl halide at room temperature or under cooling. The reaction is usually carried out in a solvent and examples of such a solvent are halogenated hydrocarbons, such as chloroform, carbon tetrachloride, dichloroethane, methylene chloride, etc.; aromatic hydrocarbons such as benzene, toluene, xylene, etc.; and chain or cyclic ethers such as ether, tetrahydrofuran, dioxane, etc. The reaction may be carried out in the presence of a dehydrohalogenating agent such as triethylamine, pyridine, sodium carbonate, N,N-dimethylaniline, etc.

Then, for obtaining the compound of formula III from the compound of Formula II thus formed, the compound may be reacted with a dehydrohalogenating agent in an organic solvent. As the organic solvent in the reaction, alcohols such as methanol, ethanol, isopropanol, etc., may be applied in addition to the aforesaid various organic solvents used in the first stage reaction. Also, examples of the dehydrohalogenating agent used in the reaction are sodium methylate, potassium ethylate, sodium hydride, sodium amide, etc. The reaction is usually carried out under heating to about 50°–100° C. for about 5–6 hours. The compound of formula II in the reaction mixture may be used in the next reaction step without isolation.

The reaction for obtaining the subject compound of formula IV from the compound of formula III is performed as follows. That is, the compound of formula III is dissolved in an organic solvent such as ethers, e.g., ether, tetrahydrofuran, dioxane, etc., and alcohols, e.g., methanol, ethanol, etc., and then a slightly excessive amount of a metal hydride complex, such as lithium aluminum hydride, bis(methoxyethoxy) lithium aluminum hydride, sodium borohydride, etc., is added to the solution. The reaction solvent and metal complex compound may be properly selected according to the properties of the reaction solvent and the metal complex compound.

The subject compound of formula IV thus obtained can be isolated and purified by an ordinary method such as filtration, concentration, extraction, column chromatography, etc., after adding a small amount of water to the reaction mixture to decompose the excessive complex metal hydride compound remaining therein.

In another embodiment for producing the compound of formula IV of this invention, the compound represented by general formula V

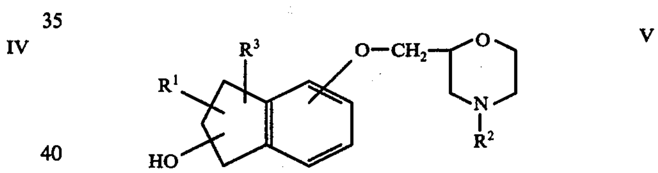

wherein $R^1$ and $R^2$ and $R^3$ have the same meaning as in general formula IV and said $R^1$ is bonded to the same carbon atom to which the hydroxy group is bonded is dehydrated under heating in the presence or absence of a catalyst.

For carrying out the reaction, the compound of formula V is heated in solvent such as xylene, toluene, benzene, dimethyl sulfoxide, dioxane, methanol, ethanol, etc. When, in this case, a catalytic amount of an acid such as p-toluenesulfonic acid, benzene-sulfonic acid, hydrogen chloride, hydrogen bromide, concentrated sulfuric acid, etc., is added to the reaction system, the reaction proceeds more smoothly. The reaction temperature is not specially limited, and the reaction is usually carried out near the boiling point of a solvent.

In another preferred embodiment for producing the compound of formula IV of this invention, a 1,2-epoxy-3-indenyloxypropane of the general formula VI:

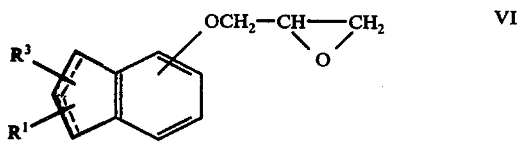

wherein $R^1$, $R^3$ have the same meanings as in general formula IV, is reacted with an amine compound of the formula VII:

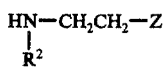

wherein $R^2$ has the same meaning as in general formula IV, Z is a halogen atom or $—OSO_3R^4$ (wherein $R^4$ is a hydrogen atom, an aryl group, or a lower alkyl group), whereby the morpholine derivatives of the general formula IV:

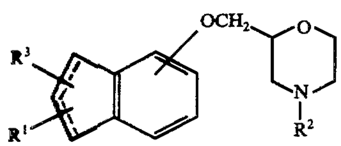

wherein $R^1$-$R^3$ have the same meaning as above, are obtained. Further, the aryl groups within the scope of $R^4$ in the compound VII are, for example, a phenyl group and p-tolyl group, etc.

The preparation of the 2-(indenyloxymethyl)morpholines of Formula (IV) may be accomplished by reacting the appropriate 1,2-epoxy-3-indenyloxypropane (VI) with an amine compound (VII), in the presence of a basic substance such as, for example, an alkali metal hydroxide, an alkaline earth metal hydroxide such as sodium hydroxide, potassium hydroxide, barium hydroxide, calcium hydroxide, in a solvent such as water, methanol, ethanol, isopropanol, n-butanol, tert-butanol, ethylene glycol, tetrahydrofuran, dioxane or mixtures thereof at or above room temperature.

A most suitable compound of this invention is the acid addition salt of 2-(7-indenyloxymethyl) morpholine of the following formula IV -1'

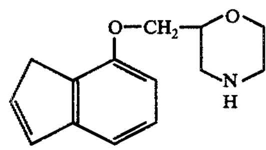

The preferred embodiment for preparing compound IV-1' is as follows:

That is, 1,2-epoxy-3-(7-indenyloxy)propane and/or 1,2-epoxy-3-(4-indenyloxy) propane of the formula VI-1

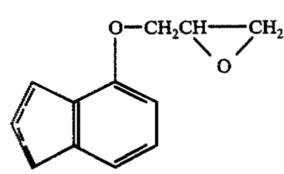

wherein the dotted lines have the same meaning as in the aforesaid formula are reacted with an amine compound of the formula VII

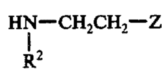

in the presence of a base to produce a mixture of a 2-(7-indenyloxymethyl)morpholine compound and a 2-(4-indenyloxymethyl)morpholine compound of the formula IV-2,

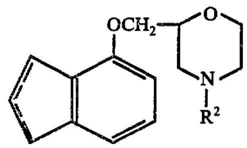

wherein $R^2$ and the dotted lines have the same meanings as above. There is then added to the mixture that is obtained a suitable acid as illustrated hereinafter in an amount slightly less than the stoichiometric amount to isomerize the 2-(4-indenyloxymethyl) morpholine compound, whereby the acid addition salt of the 2-(7-indenyloxymethyl)morpholine compound of the formula IV-1

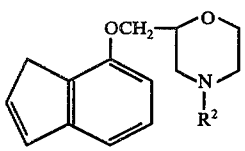

wherein $R^2$ has the same meaning as above, is obtained.

The subject compound of formula IV obtained can be isolated and purified by the aforesaid method.

The compound of formula IV may be converted, if desired, into the salt thereof with an inorganic acid such as hydrochloric acid, hydrobromic acid, phosphoric acid, sulfuric acid, etc., or an organic acid such as acetic acid, fumaric acid, maleic acid, oxalic acid, citric acid, tartaric acid, glutamic acid, ascorbic acid, etc.

Furthermore, in the indene ring of the starting material (I) and the subject compound (IV), the contamination due to tautomer is estimated since there exists a possibility of prototropy or migration of the double bond under basic conditions [Tetrahedron, 21, 490 (1965)] when the substituents at 1- and 3-position of the indene ring are both hydrogen atoms or each represents lower alkyl group or phenyl group.

For example, the compound obtained in Example 10 is a mixture of the 2-(4-indenyloxymethyl)morpholine compound (hereinafter referred to as the 4-isomer) and 2-(7-indenyloxymethyl)morpholine compound (hereinafter referred to as the 7-isomer). From the acid addition salts of this mixture (for example, the hydrochloric acid salt or the maleic acid salt etc.), each of the 7-isomer and the 4-isomer can be separated and recovered by fractional recrystallization. In this fractional recrystallization, an organic solvent such as methanol and isopropanol is used.

Further, the acid addition salt of the tautomeric mixture of the above two isomers showed an unexpected property in that the 4-isomer is isomerized into the 7-isomer in the presence of a small amount of a base. Hence, only the 7-isomer can be obtained as the acid addition salt thereof by isomerizing the mixture of the both isomers (free bases) obtained by this reaction as it is, or after purification by adding thereto, in an organic solvent, an acid in an amount slightly less than the stoichiometric amount to act thereto the remaining free base itself as the base, or by adding to the mixture of the isomers, an acid in a stoichiometric amount or an amount slightly in excess of the stoichiometric amount to convert the whole isometric mixture into acid addition salts and then adding a small amount of a basic material to the salts in an organic solvent. The purification of the mixture of the isomers can be performed by a conventional method such as, for example, filtration, concentration, extraction, distillation, column chromatography, recrystallization, etc. Suitable acids used in forming the acid addition salts of the isomers include, for example, organic acids such as citric acid, acetic acid, lactic acid, maleic acid, fumaric acid, benzoic acid, tartaric acid, ascorbic acid, succinic acid, malic acid, and the like, and inorganic acids such as hydrochloric acid, sulfuric acid, phosphoric acid, nitric acid, and the like. Further, suitable basic materials used in the isomerization include for example, a free tautomeric mixture and other organic and inorganic bases such as pyridine, triethylamine, sodium hydroxide, barium hydroxide, and the like.

Furthermore, after converting the aforesaid mixture of isomers into the mixture of the acid addition salts of the isomers by adding to the isomer mixture, as it is or after purification, a stoichiometric amount or a slightly excessive amount of an acid, the acid addition salt of the 7-isomer and the acid addition salt of the 4-isomer can be separated and recovered by fractional recrystallization. For the fractional recrystallization, an organic solvent such as methanol and isopropanol is used.

The compounds of this invention (IV-1) show methamphetamine stereotyped increasing activity which is one of the desired pharmacological properties as an antidepression agent and further the activity is stronger than that of the known antidepression agent, Amitriptyline.

The compounds of this invention (IV-1) also show antireserpine activity which is one of desired pharmacological properties as an antidepression agent and such compounds are characterized by higher activity than known compounds.

The acute toxicity of the compound of this invention (IV-1) on oral administration, is only about ½ of known compounds and the compounds of this invention (IV-1) show an excellent safety coefficient in medical treatment particularly in view of potential activities of the compounds.

The compounds of this invention (IV-1) further show higher activities in potentiating the effect of 5-hydroxytryptophan which is one of the desirable effects as an antidepression agent, as compared, for example, with known compounds, Amitriptyrine and Imipramine.

In addition, the isolated 7-isomer acid addition salt shows a more preferable pharmacological activity than the 4-isomer acid addition salt.

Moreover, in the isomerization reaction, it is unnecessary to dissolve the tautomeric mixture (free bases, acid addition salts) in a solvent, i.e., the tautomeric mixture may remain as it is in the reaction system and complete dissolution is not required.

The subject compound of this invention can be orally or parenterally administered, for example, by the form of powder, granules, tablets, capsules, injections, suppository, etc. The dosage of the compound for an adult is 50–300 mg./day but the dosage may be varied suitably according to the age, health condition, disease condition, etc. of the patient.

Experiment 1

Effects of the compounds on methamphetamine-induced stereotyped behavior in rats (male Wistar strain, aged 6 weeks) were examined according to the method of Ueki et al. (Folia Pharmacologica Japonica, 68, 716, 1972).

The rats were placed in separate plastic cages for 1 hour to be accustomed to the experimental conditions, then the tested compounds were given intraperitoneally followed after 1 hour by an intraperitoneal application of methamphetamine (5 mg/Kg). The influences of the tested compounds on agitated behavior of the rats were observed every 30 minutes until 5 hours thereafter. The minimum effective doses which caused a statistically significant potentiation of the methamphetamine-induced stereotype are presented in the following table.

Table

| Compound (shown by example No.) | Dose (mg/Kg, i.p.) |
|---|---|
| 1 | 0.3 |
| 2 | 3 |
| 5 | 0.3 |
| 6 | 1 |
| 10 | 0.3 |
| 11 | 0.3 |
| 12A | 0.03 |
| 12B | 0.3 |
| Amitriptyline (control) | 10 |
| Viloxazine HCl (control) | non effective |
| Compound C * (control) | non effective |

* Compound C: 2-(4-indanyloxymethyl)-4-isopropyl morpholine

Experiment 2

Effects of the compounds on reserpine-induced hypothermia in mice (male ICR-JCL strain, aged 5 weeks) were investigated by the method of Ueki et al.

The mice were pretreated with reserpine (3 mg/Kg, s.c.) and were housed in separate plastic cages for 17 hours. The room temperature was kept at 23±1° C. The tested compounds (1 mg/Kg) were given orally and the rectal temperature of the mice were measured 5 hours thereafter. The raise of temperature is indicated in the following Table. For each compound 10 mice were used.

Table

| Compound (shown by example No.) | Change in rectal temperature (° C) |
|---|---|
| 1 | + 2.30 |
| 3 | + 2.07 |
| 6 | + 3.14 |
| Viloxazine HCl (control) | + 1.92 |
| Compound C (control) | + 1.14 |

Experiment 3

Competitive effects of the compounds on reserpine induced ptoses and hypothermia in mice (male ICR-JCL strain weighing 25–35 g) were tested.

The tested compound (10 mg/Kg, p.c.) and reserpine (2 mg/Kg, i.p.) were applied simultaneously to the mice and the degree of ptosis was scored according to the method of Ruben et al. (J. Pharmacol. Exptl. Ther., 120, 125, 1957) at 0.5, 1, 2, 3, 4, 5 and 6 hours after dosages, respectively.

Rectal temperature of the mice were also measured together with those of non-reserpinized mice. Inhibitory percent of the degree of ptosis and differences between rectal temperatures of reserpinized and non-reserpinized mice due to the tested compound are shown in the following Table. For each experiment 10 mice were used.

Table

| Compound (shown by example No.) | Inhibition of ptosis (%) | Change in rectal temperature |
|---|---|---|
| 1 | 14.5 | + 1.5 |
| Viloxazine HCl (control) | 6.0 | + 0.2 |

Experiment 4

Potentiation of the effects of DL-5-hydroxytriptophan (5HTP) was examined in mice (male ICR-JCL strain, weighing 25–35 g).

5HTP (90 mg/Kg, i.v.) was injected intravenously 1 hour after the treatment with the tested compound. Behaviors of the mice were observed for 1 hour and the minimum effective doses of the compounds which produced tremor, abduction of hind limbs or head twitch in the test animals were determined using 6 to 10 mice for each dose level. The results are shown below.

Table

| Compound (shown by example No.) | Minimum Effective Dose (mg/Kg, i.p.) |
|---|---|
| 1 | 25 |
| 3 | 50 |
| 10 | 15 |
| Amitriptyline (control) | 25 |
| Imipramine (control) | 50 |
| Viloxazine HCl (control) | non effective (5–100 mg/Kg) |

Experiment 5

Acute toxicity (ICR-JCR strain, male, weighing 25–35 g, p.o.)

Table

| Compound (shown by example No.) | $LD_{50}$ (mg/Kg) |
|---|---|
| 1 | 650 |
| 5 | 700 |
| Viloxazine HCl (control) | 380 |

From the above described experimental results, it will be understood that the subject compounds of this invention are useful compounds having the following features:

(1) the compounds of this invention showed methamphetamine stereotyped increasing activity which is one of the desired pharmacological properties as an antidepression agent and further the activity was stronger than that of the known antidepression agent, Amitriptyline.

(2) the compounds of this invention showed antireserpine activity, which is also one of desired pharmacological properties as an antidepression agent, stronger than known compounds.

(3) since the acute toxicity of the compounds of this invention at oral administration was about one-half of known compounds, the compounds of this invention showed excellent safety coefficient in medical treatment on considering the strong activities of the compounds.

(4) the compounds of this invention show higher activities in the potentiation of the effect of 5-hydroxytryptophan, which is one of the desirable effects as antidepression agents, than those of known compounds, Amitriptyline and Imipramine.

Experiment 6

Effects of the compounds on methamphetamine-induced stereotyped behavior in rats (male Wistar strain, aged 8 weeks) were examined according to the method of Ueki et al. (Folia Pharmacologica Japonica, 68, 716, 1972).

The rats were placed in separate plastic cages for 1 hour to be accustomed to the experimental conditions and then the tested compounds were given intraperitoneally followed, after 1 hour, by an intraperitoneal application of methamphetamine (5 mg/kg). The influence of the tested compounds on the agitated behavior of the rats were observed every 30 minutes till 5 hours thereafter.

The $ED_{50}$ of the tested compounds were 12.5 mg/Kg. and 5 mg/Kg. i.p. with respect to 2-(7-indenyloxymethyl) morpholine hydrochloride and 2-(4-indenyloxymethyl) morpholine hydrochloride, respectively. The former was 2.5 times as potent as the latter.

Experiment 7

Effects of the compounds on reserpine-induced hypothermia in mice (male ICR-JCL strain, aged 5 weeks) were investigated by the method of Ueki et al. (ibid). The mice were pretreated with reserpine (3 mg/Kg s.c.) and were housed in separate plastic cages for 17 hours. The room temperature was kept at 23±1° C. The tested compounds were given orally and the rectal temperature of the mice was measured 5 hours thereafter. The differences of the rectal temperature (ΔT) in the rats to those of the control group, and the sum of the differences (εΔT) were calculated, followed by a graphical estimation of $ED_{T=1.5° C}$. $ED_{T=1.5° C}$ of 2-(7-indenyloxymethyl)morpholine hydrochloride and 2-(4-indenyloxymethyl) morpholine hydrochloride were 1.8 mg/Kg and 2.4 mg/Kg p.o., respectively. The former proved to be more potent than the latter in their efficacy.

The following examples will serve to illustrate the present invention.

EXAMPLE 1

(a) In 30 ml. of dichloromethane were dissolved 2.5 g. (0.01 mole) of 7-(2-hydroxy-3-isopropylaminopropoxy)indene and 1.2 g (0.013 mole) of triethylamine and after cooling the solution to 0°-5° C, 2.0 g (0.01 mole) of bromoacetyl bromide was added dropwise to the solution with stirring. After 30 minutes, the mixture was further stirred for 6 hours at room temperature. Then, the reaction mixture was washed with an aqueous 5% hydrochloric acid solution and then water and dried over anhydrous magnesium sulfate.

After drying, the solvent was distilled off under reduced pressure to provide 7-(3-N-bromoacetyl-N-isopropylamino-2-hydroxypropoxy)indene. In 30 ml. of anhydrous methanol was dissolved 3.6 g. of the product and after adding to the solution a solution prepared by dissolving 0.3 g. of metallic sodium in 20 ml. of anhydrous methanol, the mixture was refluxed for 6 hours with stirring. Methanol was distilled off from the reaction mixture, the residue formed was dissolved in 50 ml. of chloroform, and the solution was washed twice each with 10 ml. of an aqueous 10% hydrochloric acid solution and then twice each with 10 ml. of water successively and dried over anhydrous magnesium sulfate. Thereafter, the solvent was distilled off under reduced pressure and the residue formed was dissolved in a small amont of ethyl acetate. The solution was subjected to a silica gel column chromatography (column diameter 1.5 cm., height 20 cm., and eluting solution 150 ml.) and the eluting solution were collected and concentrated to provide 2.5 g. (yield 86%) of oily 2-(7-indenyloxymethyl)-4-isopropylmorpholin-5-one.

Elemental analysis for $C_{17}H_{21}O_3N$:

| | C | H | N |
|---|---|---|---|
| Calculated: | 71.06% | 7.37% | 4.87% |
| Found: | 71.37% | 7.51% | 4.90% |

Nuclear magnetic resonance spectrum ($CDCl_3$, ppm):

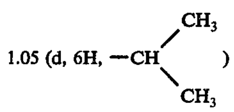

(b). In 50 ml. of anhydrous tetrahydrofuran was suspended 0.5 g. of lithium aluminum hydride and after adding slowly to the suspension a solution of 2.0 g. of 2-(7-indenyloxymethyl)-4-isopropylmorpholin-5-one in 10 ml. of anhydrous tetrahydrofuran with stirring, the mixture was stirred for 10 hours at 40°-50° C. Then, to the reaction mixture thus formed were added 0.5 ml. of water, 0.5 ml. of an aqueous 15% sodium hydroxide solution, and then 1.5 ml. of water successively to decompose excess lithium aluminum hydride. After stirring the mixture for 30 minutes, the mixture was filtered and the filtrate was concentrated under reduced pressure. The residue formed was dissolved in a small amount of ethyl acetate and the solution was subjected to a silica gel column chromatography (column diameter 1.5 cm., height 10 cm., eluting solution 200 ml.) to provide 1.5 g. (yield 79%) of oily 4-isopropyl-2-(7-indenyloxymethyl)morpholine.

Elemental analysis for $C_{17}H_{23}O_2N$:

| | C | H | N |
|---|---|---|---|
| Calculated: | 74.69% | 8.48% | 5.12% |
| Found: | 74.41% | 8.23% | 4.98% |

Nuclear magnetic resonance spectra ($CDCl_3$, ppm):

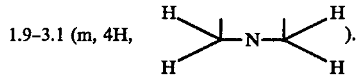

In addition, the citrate of the product showed a melting point of 107°-109° C.

EXAMPLE 2

(a). In 100 ml. of dichloroethane were dissolved 8.9 g. (0.034 mole) of 7-(3-butylamino-2-hydroxypropoxy)indene and 3.42 g. (0.034 mole) of triethylamine and after cooling the solution to 0°-5° C., 6.8 g. (0.034 mole) of bromoacetyl bromide was added dropwise to the solution with stirring.

Then, by treating the mixture in a similar manner as in Example 1, 12.9 g. of oily 7-(3-N-bromoacetyl-N-butylamino-2-hydroxypropoxy)indene was obtained. The product was dissolved in 100 ml. of anhydrous methanol and after adding to the solution thus formed a solution prepared by dissolving 0.8 g. of metallic sodium in 100 ml. of anhydrous methanol, the mixture was refluxed for 6 hours. Then, methanol was distilled off from the reaction mixture and the residue formed was dissolved in 150 ml. of chloroform. The solution was washed twice each with 30 ml. of an aqueous 10% hydrochloric acid solution and then twice each with 30 ml. of water and thereafter dried over anhydrous magnesium sulfate. Then, the solvent was distilled off from the solution under reduced pressure and the residue formed was treated in a similar manner as in Example 1 to provide 8.0 g. (yield 78%) of oily 4-butyl-2-(7-indenyloxymethyl)morpholin-5-one.

Elemental analysis for $C_{18}H_{23}O_3N$:

| | C | H | N |
|---|---|---|---|
| Calculated: | 71.73% | 7.69% | 4.65% |
| Found: | 71.46% | 7.38% | 4.59% |

Nuclear magnetic resonance spectra ($CDCl_3$, ppm): 0.9 (t, 3H, $—CH_3$); 1.1-1.7 (m. 4H, $—CH_2—CH_2—CH_3$); 2.32 (t, 2H, $—CH_2—(CH_2)_2CH_3$).

(b). In 250 ml. of anhydrous tetrahydrofuran was suspended 2.0 g. of lithium aluminum hydride and then a solution prepared by dissolving 8.0 g. of 4-butyl-2-(7-indenyloxymethyl)morpholin-5-one in 50 ml. of anhydrous tetrahydrofuran was added slowly to the suspension with stirring. Then, by treating the mixture in a similar manner as in Example 1, 6.4 g. (yield) of oily 4-butyl-2-(7-indenyloxymethyl)-morpholine was obtained.

Elemental analysis for $C_{18}H_{25}O_2N$:

| | C | H | N |
|---|---|---|---|
| Calculated: | 75.23% | 8.77% | 4.87% |
| Found: | 75.20% | 8.61% | 4.70% |

Nuclear magnetic resonance spectra ($CDCl_3$, ppm):

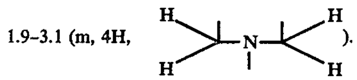

EXAMPLE 3

(a). In 60 ml. of dichloromethane were dissolved 4.4 g. (0.02 mole) of 7-(2-hydroxy-3-methylaminopropoxy)indene and 2.05 g. (0.02 mole) of triethylamine and after cooling the solution to 0°-5° C., 4.05 g. (0.02 mole) of bromoacetyl bromide was added to the solution with stirring. Then, by treating the mixture in a similar manner as in Example 1, 7.0 g. of oily 7-(3-N-bromoacetyl-N-methylamino-2-hydroxypropoxy)indene was obtained. The product was dissolved in 70 ml. of anhydrous methanol and after adding thereto a solution prepared by dissolving 0.5 g. of metallic sodium in 50 ml. of anhydrous methanol, the mixture was refluxed for 6 hours. Then, methanol was distilled off from the reaction mixture, the residue formed was dissolved in 50 ml. of chloroform, and the solution thus formed was washed twice each with 10 ml. of an aqueous 10% hydrochloric acid solution and then twice each with 10 ml. of water, and dried over anhydrous magnesium sulfate. The solvent was distilled off from the mixture and the residue formed was treated in a similar manner as in Example 1 to provide 4.1 g. (yield 79%) of oily 2-(7-indenyloxymethyl)-4-methylmorpholin-5-one.

Elemental analysis for $C_{15}H_{17}O_3N$:

| | C | H | N |
|---|---|---|---|
| Calculated: | 69.48% | 6.61% | 5.40% |
| Found: | 69.19% | 6.36% | 5.35% |

Nuclear magnetic resonance spectrum ($CDCl_3$, ppm): 2.28 (s, 3H, $CH_3$).

(b). In 200 ml. of anhydrous tetrahydrofuran was suspended 1.4 g. of lithium aluminum hydride and after adding thereto slowly a solution prepared by dissolving 5.8 g. of 2-(7-indenyloxymethyl)-4-methylmorpholin-5-one in 30 ml. of tetrahydrofuran, the mixture was treated in a similar manner as in Example 1 to provide 2.1 g. (yield 38%) of oily 2-(7-indenyloxymethyl)-4-methylmorpholine.

Elemental analysis for $C_{15}H_{19}O_2N$:

| | C | H | N |
|---|---|---|---|
| Calculated: | 73.44% | 7.81% | 5.71% |
| Found: | 73.59% | 7.93% | 5.69% |

Nuclear magnetic resonance spectra ($CDCl_3$, ppm):

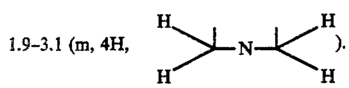

EXAMPLE 4

(a). In 300 ml. of dichloromethane were dissolved 20 g. (0.068 mole) of 7-(3-benzylamino-2-hydroxypropoxy)indene and 6.9 g. (0.068 mole) of triethylamine and after cooling the solution to 0°-5° C., 10.7 g. (0.068 mole) of bromoacetyl chloride was added dropwise to the solution with stirring. Then, by treating the mixture in a similar manner as in Example 1, 27.5 g. of oily 7-(3-N-benzyl-N-bromoacetyl-2-hydroxypropoxy)indene was obtained.

The oily product obtained was dissolved in 100 ml. of anhydrous methanol and after adding thereto a solution prepared by dissolving 1.52 g. of metallic sodium in 300 ml. of anhydrous methanol, the mixture was refluxed for 6 hours. Then, methanol was distilled off from the reaction mixture, the residue formed was dissolved in 200 ml. of chloroform, and the solution was washed twice each with 50 ml. of an aqueous 10% hydrochloric acid solution and then twice each with 50 ml. of water, and dried over anhydrous magnesium sulfate. The solvent was distilled off and the oily material formed was dissolved in a small amount of ethyl acetate. Then, by treating the solution thus obtained in a similar manner as in Example 1, 20.8 g. (yield 91.5%) of oily 4-benzyl-2-(7-indenyloxymethyl)morpholin-5-one was obtained.

Elemental analysis for $C_{21}H_{21}O_3N$:

| | C | H | N |
|---|---|---|---|
| Calculated: | 75.20% | 6.31% | 4.18% |
| Found: | 74.91% | 6.45% | 4.40% |

Nuclear magnetic resonance spectra ($CDCl_3$, ppm):

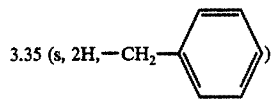

-continued

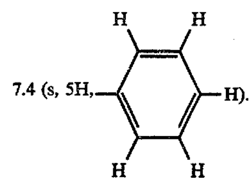

(b). In 300 ml. of anhydrous tetrahydrofuran was suspended 20 g. of lithium aluminum hydride and after adding slowly to the suspension a solution prepared by dissolving 8.0 g. of 4-benzyl-2-(7-indenyloxymethyl)-morpholin-5-one in 50 ml. of tetrahydrofuran, the mixture was treated in a similar manner as in Example 1 to provide 6.8 g. (yield 89%) of oily 4-benzyl-2-(7-indenyloxymethyl)morpholine.

Elemental analysis for $C_{21}H_{23}O_2N$:

| | C | H | N |
|---|---|---|---|
| Calculated: | 78.47% | 7.21% | 4.36% |
| Found: | 78.11% | 7.32% | 4.59% |

Nuclear magnetic resonance spectra ($CDCL_3$, ppm):

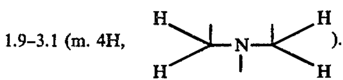

EXAMPLE 5

(a). In 50 ml. of dichloromethane were dissolved 3.5 g.(0.015 mole) of 7-(3-ethylamino-2-hydroxypropoxy)indene and 1.6 g. (0.016 mole) of triethylamine and after cooling the solution to 0°-5° C., 3.1 g. (0.015 mole) of bromoacetyl bromide was added dropwise to the solution with stirring. Then, by treating the mixture in a similar manner as in Example 1, 5.2 g. of oily 7-(3-N-bromoacetyl-N-ethylamino-2-hydroxypropoxy)indene was obtained. The oily product was then dissolved in 40 ml. of anhydrous methanol and after adding thereto a solution prepared by dissolving 0.4 g. of metallic sodium in 30 ml. of anhydrous methanol, the mixture was refluxed for 6 hours. Thereafter, methanol was distilled off from the reaction mixture, the residue formed was dissolved in 60 ml. of chloroform, and the solution was washed twice each with 15 ml. of an aqueous 10% hydrochloric acid solution and then twice each with 15 ml. of water and dried over anhydrous magnesium sulfate. The solvent was then distilled off under reduced pressure and the residue formed was dissolved in a small amount of ethyl acetate. Then, by treating the solution in a similar manner as in Example 1, 3.6 g. (yield 86%) of oily 4-ethyl-2-(7-indenyloxymethyl)morpholin-5-one was obtained.

Elemental analysis for $C_{16}H_{19}O_3N$:

| | C | H | N |
|---|---|---|---|
| Calculated: | 70.31% | 7.01% | 5.12% |
| Found: | 70.10% | 6.84% | 5.08% |

Nuclear magnetic resonance spectra ($CDCl_3$, ppm): 2.42 (q. 2H, $-CH_2-CH_3$) and 1.08 (t, 3H, $-CH_2-CH_3$).

(b). In 250 ml. of anhydrous tetrahydrofuran was suspended 1.8 g. of lithium aluminum hydride and after adding slowly to the suspension a solution prepared by dissolving 7.5 g. of 4-ethyl-2-(7-indenyloxymethyl)morpholin-5-one in 60 ml. of tetrahydrofuran, the mixture was treated in a similar manner as in Example 1 to provide 6.5 g. of oily 4-ethyl-2-(7-indenyloxymethyl)morpholine.

Elemental analysis for $C_{16}H_{21}O_2N$:

| | C | H | N |
|---|---|---|---|
| Calculated: | 74.10% | 8.16% | 5.40% |
| Found: | 73.83% | 7.99% | 5.41% |

Nuclear magnetic resonance spectra ($CDCl_3$, ppm):

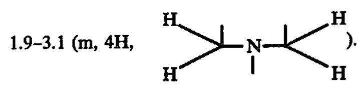

EXAMPLE 6

(a). In 60 ml. of dichloromethane were dissolved 5.0 g. (0.02 mole) of 4-(2-hydroxy-3-propylaminopropoxy)indene and 2.4 g. (0.024 mole) of triethylamine and after cooling the solution to 0°-5° C., 4.0 g. (0.02 mole) of bromoacetyl bromide was added dropwise to the solution with stirring. Then, by treating the mixture in a similar manner as in Example 1, 7.3 g. of oily 7-(3-N-bromoacetyl-N-propylamino-2-hydroxypropoxy)indene was obtained. The product was dissolved in 60 ml. of anhydrous methanol and after adding thereto a solution prepared by dissolving 0.6 g. of metallic sodium in 40 ml. of anhydrous methanol, the mixture was refluxed for 6 hours. Then, methanol was distilled off from the reaction mixture, the residue formed was dissolved in 100 ml. of chloroform, and the solution formed was washed twice each with 20 ml. of an aqueous 10% hydrochloric acid solution and then twice each with 20 ml. of water, and dried over anhydrous magnesium sulfate. The solvent was then distilled off from the solution and the oily material formed was dissolved in a small amount of ethyl acetate. Then, by treating the solution in a similar manner as in Example 1, 5.1 g. (yield 88%) of oily 2-(7-indenyloxymethyl)-4-propylmorpholine-5-one was obtained.

Elemental analysis for $C_{17}H_{21}O_3N$:

| | C | H | N |
|---|---|---|---|
| Calculated: | 71.06% | 7.37% | 4.81% |
| Found: | 70.94% | 7.10% | 4.57% |

Nuclear magnetic resonance spectra ($CDCl_3$, ppm): 0.9 (t, 3H, $-CH_2CH_2CH_3$); 1.45 (m, 2H, $-CH_2-CH_2-CH_3$); 2.22 (t, 2H, $-CH_2-CH_2-CH_3$)

(b). In 50 ml. of anhydrous tetrahydrofuran was suspended 0.5 g. of lithium aluminum hydride and after adding slowly to the suspension a solution prepared by dissolving 2.0 g. of 2-(7-indenyloxymethyl)-4-propylmorpholin-5-one in 10 ml. of anhydrous tetrahydrofuran, the mixture was treated in a similar manner as in Example 1 to provide 1.7 g. (yield 89.5%) of oily 2-(7-indenyloxymethyl)-4-propylmorpholine.

Elemental analysis for $C_{17}H_{23}O_2N$:

| | C | H | N |
|---|---|---|---|
| Calculated: | 74.69% | 8.48% | 5.12% |
| Found: | 74.33% | 8.19% | 5.05% |

Nuclear magnetic resonance spectra ($CDCl_3$, ppm):

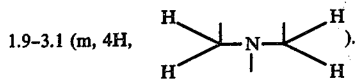

EXAMPLE 7

(a). In 150 ml. of dichloroethane were dissolved 10.0 g. of 7-(3-tert-butylamino-2-hydroxypropoxy)indene and 3.9 g. of triethylamine and after cooling the solution to 0°-5° C., 7.7 g. of bromoacetyl bromide was added dropwise to the solution with stirring. After 30 minutes, the mixture was further stirred at room temperature for 6 hours. The reaction mixture was then washed with an aqueous 5% hydrochloric acid solution and water successively and dried over anhydrous magnesium sulfate. Thereafter, the solvent was distilled off under reduced pressure to provide 7-(3-N-bromoacetyl-N-tert-butylamino-2-hydroxypropoxy)indene. The product (11.5 g.) was dissolved in 50 ml. of anhydrous methanol and after adding thereto a solution prepared by dissolving 0.7 g. of metallic methanol in 70 ml. of absolute methanol, the mixture was refluxed for 6 hours with stirring. Then, methanol was distilled off from the reaction mixture, the residue formed was dissolved in 200 ml. of chloroform, and the solution was washed twice each with 50 ml. of an aqueous hydrochloric acid solution and then twice each with 50 ml. of water, and dried over anhydrous magnesium sulfate. Then, the solvent was distilled off from the chloroform solution under reduced pressure and the residue formed was purified by silica gel column chromatography (column diameter 2 cm., height 30 cm.) using ethyl acetate as the eluting solution. The eluates were collected and concentrated to provide 5.3 g. (yield 46%) of oily 4-tert-butyl-2-(7-indenyloxymethyl)morpholin-5-one.

Elemental analysis for $C_{18}H_{23}O_3N$:

| | C | H | N |
|---|---|---|---|
| Calculated: | 71.73% | 7.69% | 4.65% |
| Found: | 71.51% | 7.46% | 4.55% |

(b). In 100 ml. of anhydrous tetrahydrofuran was suspended 1.0 g. of lithium aluminum hydride and after adding slowly to the suspension with stirring a solution prepared by adding 4.0 g. of 4-tert-butyl-2-(7-indenyloxymethyl)morpholin-5-one in 20 ml. of anhydrous tetrahydrofuran, the mixture was stirred overnight at room temperature. Then, to the reaction mixture were added 1 ml. of water, 1 ml. of an aqueous 15% sodium hydroxide solution, and then 3 ml. of water successively to decompose excessive lithium aluminum hydride. The mixture was further stirred for 30 minutes and then filtered. The filtrate was concentrated under reduced pressure and the residue formed was dissolved in a small amount of ethyl acetate. The product was purified by silica gel column chromatography (diameter 1.5 cm., height 20 cm.) to provide 2.3 g. of oily 4-tert-butyl-2-(7-indenyloxymethyl)morpholine.

Elemental analysis for $C_{18}H_{25}O_2N$:

| | C | H | N |
|---|---|---|---|
| Calculated: | 75.23% | 8.77% | 4.87% |
| Found: | 75.39% | 8.78% | 4.90% |

Nuclear magnetic resonance spectrum: ($CDCl_3$, ppm):

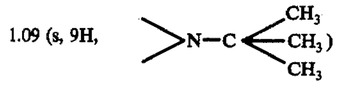

The citrate of the product showed a melting point of 114°-116° C.

EXAMPLE 8

(a). In 150 ml. of dichloroethane were dissolved 12.0 g. of 7-(3-cyclohexylamino-2-hydroxypropoxy)indene and 4.2 g. of triethylamine and after cooling the solution to 0°-5° C., 8.4 g. of bromoacetyl bromide was added dropwise to the solution with stirring. Then, by treating the mixture in a similar manner as in Example 7-(a), 16.2 g. of 7-(3-N-bromoacetyl-N-cyclohexylamino-2-hydroxypropoxy)indene was obtained. The product was dissolved in 80 ml. of anhydrous methanol and after adding thereto a solution prepared by dissolving 0.9 g. of metallic sodium in 100 ml. of anhydrous methanol, the mixture was refluxed for 6 hours with stirring. Then, methanol was distilled off from the reaction mixture and the residue formed was dissolved in 200 ml. of chloroform. The solution was washed twice each with 50 ml. of an aqueous 10% hydrochloric acid solution and then twice each with 50 ml. of water and then dried over anhydrous magnesium sulfate. The solvent was then distilled off from the chloroform solution under reduced pressure and the residue formed was recrystallized from methanol to provide 11.3 g. of 4-cyclohexyl-2-(7-indenyloxymethyl)morpholin -5-one having a melting point of 106°-107° C.

Elemental analysis for $C_{20}H_{25}O_3N$:

| | C | H | N |
|---|---|---|---|
| Calculated: | 73.37% | 7.70% | 4.28% |
| Found: | 73.08% | 7.51% | 4.00% |

(b). In 150 ml. of anhydrous tetrahydrofuran was suspended 1.25 g. of lithium aluminum hydride and after adding slowly to the suspension with stirring a solution prepared by dissolving 5.0 g. of 4-cyclohexyl-2-(7-indenyloxymethyl)morpholin -5-one in 30 ml. of anhydrous tetrahydrofuran, the mixture was stirred overnight at room temperature. To the reaction mixture were added successively 1.25 ml. of water, 1.25 ml. of a 15% sodium hydroxide aqueous solution and then 3.75 ml. of water to decompose excess lithium aluminum hydride.

Then, by treating the mixture in a similar manner as in Example 7-(b), 3.5 g. of oily 4-cyclohexyl-2-(7-indenyloxymethyl)morpholine was obtained.

Elemental analysis for $C_{20}H_{27}O_2N$:

| | C | H | N |
|---|---|---|---|
| Calculated: | 76.64% | 8.68% | 4.47% |
| Found: | 76.73% | 8.67% | 4.53% |

Nuclear magnetic resonance spectra ($CDCl_3$, ppm):

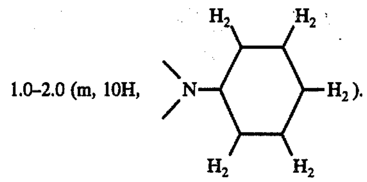

EXAMPLE 9

(a). In 150 ml. of dichloroethane were dissolved 15.0 g. of 7-(3-anilino-2-hydroxypropoxy)indene and 5.4 g. of triethylamine and after cooling the solution to 0°-5° C., 10.7 g. of bromoacetyl bromide was added dropwise to the solution with stirring. Then, by treating the solution in a similar manner as in Example 7-(a), 21.0 g. of 7-(3-N-bromoacetyl-N-phenylamino-2-hydroxypropoxy)indene was obtained. The product was dissolved in 100 ml. of anhydrous methanol and after adding thereto a solution prepared by dissolving 1.3 g. of metallic sodium in 100 ml. of anhydrous methanol, the mixture was refluxed for 6 hours with stirring. Then, methanol was distilled off from the reaction mixture and the residue formed was dissolved in 200 ml. of chloroform. The solution was washed twice each with 50 ml. of an aqueous 10% hydrochloric acid solution and then twice each with 50 ml. of water and dried over anhydrous magnesium sulfate. Then, the solvent was distilled off from the chloroform solution under reduced pressure and the residue formed was purified by means of a silica gel column chromatography (diameter 2.0 cm., height 50 cm.) using chloroform as an eluting solution. The eluate (about 200 ml.) collected was concentrated to provide 14.5 g. of oily 2-(7-indenyloxymethyl)-4-phenylmorpholin-5-one.

Elemental analysis for $C_{20}H_{19}O_3N$:

| | C | H | N |
|---|---|---|---|
| Calculated: | 74.75% | 5.96% | 4.36% |
| Found: | 74.99% | 6.07% | 4.03% |

(b). In 200 ml. of anhydrous tetrahydrofuran was suspended 3.0 g. of lithium aluminum hydride and after adding slowly to the suspension with stirring a solution prepared by dissolving 14.5 g. of 2-(7-indenyloxymethyl)-4-phenylmorpholin -5-one in 100 ml. of anhydrous tetrahydrofuran, the mixture was stirred overnight at room temperature. To the reaction mixture obtained were added successively 3 ml. of water, 3 ml. of a 15% sodium hydroxide aqueous solution, and then 9 ml. of water to decompose excessive lithium aluminum hydride. Then, by treating the solution in a similar manner as in Example 7-(b), 10.6 g. of oily 2-(7-indenyloxymethyl)-4-phenylmorpholine was obtained.

Elemental analysis of $C_{20}H_{21}O_2N$:

| | C | H | N |
|---|---|---|---|
| Calculated: | 78.15% | 6.89% | 4.56% |
| Found: | 78.33% | 6.71% | 4.44% |

Nuclear magnetic resonance spectra ($CDCl_3$ ppm):

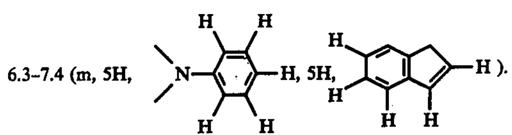

EXAMPLE 10

(a). In 120 ml. of dimethyl sulfoxide were dissolved 10 g. (0.019 mole) of 2-(p-toluenesulfonyloxymethyl)-4-triphenylmethylmorpholine and 3.6 g. (0.019 mole) of the potassium salt of 1-oxo-4-indanol and the solution formed was stirred for 17 hours at 100° C. After the reaction was over, the solvent was distilled off under reduced pressure and the residue was washed by adding thereto 15 ml. of aqueous 5% sodium hydroxide solution, whereby fine precipitates formed. The precipitates were recovered by filtration, washed with water and air-dried to provide 0.6 g. of a crude powder. By recrystallizing the powder from a 2 : 1 mixture of n-hexane and ethyl acetoacetate, the colorless acicular crystal of 2-(1-oxo-4-indanyloxymethyl)-4-triphenylmethyl morpholine melting at 213° -215 ° C. was obtained.

Elemental analysis for $C_{33}H_{31}NO_3$

| | C | H | N |
|---|---|---|---|
| Calculated: | 80.95% | 6.38% | 2.86% |
| Found: | 80.76% | 6.13% | 2.58% |

Nuclear magnetic resonance spectra ($CDCl_3$, ppm.): 6.82-7.60 (m, 18H,phenyl proton).

(b). To 1 g. of 2-(1-oxo-4-indanyloxymethyl)-4-triphenylmethyl morpholine was added 10 ml. of trifluoroacetic acid under ice-cooling to dissolve the morpholine and 10 ml. of water was immediately added to the solution followed by stirring for 15 minutes at 5°-10° C. Then, after neutralizing the reaction mixture with sodium hydrogencarbonate, the product was extracted with chloroform. Then, the extract was washed with water, dried over anhydrous magnesium sulfate, and the solvent was distilled off under reduced pressure. The sticky residue formed was subjected to a silica gel column chromatography (column diameter 3 cm., height 7 cm,) and from the fraction recovered therefrom using a 98 : 2 mixture of chloroform and methanol as an eluting solution, 0.45 g. (yield 89.1%) of sticky 2-(1-oxo-4-indanyloxymethyl)morpholine was obtained.

Elemental analysis for $C_{14}H_{17}NO_3$:

| | C | H | N |
|---|---|---|---|
| Calculated: | 67.99% | 6.93% | 5.66% |
| Found: | 67.76% | 7.01% | 5.52% |

Nuclear magnetic resonance spectra ($CDCl_3$, ppm.): 2.10 (s, 1H, >NH), 6.96-7.48 (m, 3H, phenyl proton).

(c) In 15 ml. of anhydrous tetrahydrofuran was suspended 70 mg. (0.0018 mole) of lithium aluminum hydride and after adding dropwise to the suspension with stirring at 5°-10° C. a solution prepared by dissolving 370 mg. (0.0015 mole) of 2-(1-oxo-4-indanyloxymethyl)-morpholine in 5 ml. of anhydrous tetrahydrofuran, the mixture was stirred for 3 hours at room temperature. Then, to the mixture were added successively 0.1 ml. of water, 0.1 ml. of aqueous 15% sodium hydroxide solution, and 0.3 ml. of water to decompose excessive lithium aluminum hydride. The reaction mixture was filtered and the residue was washed thrice each with 15 ml. of chloroform. The washing was combined with the filtrate obtained in the aforesaid filtration and the mixture was washed with water and dried over anhydrous magnesium sulfate. Then, by distilling off the solvent under reduced pressure, 325 mg. (yield 87.1%) of a white powder was obtained, which was recrystallized from ethyl actoacetate to provide the colorless acicular crystals of 2-(1-hydroxy-4-indanyloxymethyl)morpholine melting at 115°-117° C.

Elemental analysis for $C_{14}H_{19}NO_3$:

| | C | H | N |
|---|---|---|---|
| Calculated: | 67.44% | 7.68% | 5.62% |
| Found: | 67.03% | 7.39% | 5.44% |

Nuclear magnetic resonance spectra ($CDCl_3$, ppm.): 5.12 (t, 1H, $_{H}>C<_{OH}$), 6.60-7.25 (m, 3H, phenyl proton).

(d). In 200 ml. of anhydrous toluene was dissolved 1 g. of 2-(1-hydroxy-4-indanyloxymethyl)morpholine and after adding thereto 100 mg., of p-toluenesulfonic acid monohydrate, the mixture was refluxed for 17 hours. After cooling, the reaction mixture was washed successively with aqueous 3% sodium hydrogencarbonate and water, dried over anhydrous magnesium sulfate, and then the solvent was distilled off from the mixture under reduced pressure. The sticky residue formed was subjected to a silica gel column chromatography (diameter 3 cm., height 10 cm.) and from the fraction recovered therefrom using a 98 : 2 mixture of chloroform and methanol as an eluting solution, 530 mg. (yield 57.1%) of a sticky mixture of 2-(4-indenyloxymethyl)morpholine and 2-(7-indenyloxymethyl) morpholine was obtained. The maleate of the product was needle crystal and had a melting point of 135°-137° C.

Elemental analysis for $C_{14}H_{17}NO_2$:

| | C | H | N |
|---|---|---|---|
| Calculated: | 72.70% | 7.41% | 6.06% |
| Found: | 72.54% | 7.58% | 5.87% |

Nuclear magnetic resonance spectra ($CDCl_3$, ppm.): 1.74 (s, 1H, >NH),
6.40-7.34 (m. 5H, phenyl proton, —CH=CH—).

EXAMPLE 11

(a). To 50 ml. of anhydrous tetrahydrofuran was added 1g. (0.04 atom) of magnesium and then methyl bromide was added dropwise to the mixture at 5°-10° C. to provide a Grignard reagent. Then, a solution prepared by dissolving 2 g. (0.004 mole) of 2-(1-oxo-4-indanyloxymethyl)-4-triphenylmethyl morpholine in 20 ml. of anhydrous tetrahydrofuran was added dropwise to the reagent at 5°-10° C. Then, the mixture was stirred for 3 hours at room temperature and the solvent was distilled off under reduced pressure. The residue formed was mixed with saturated aqueous ammonium chloride solution and the mixture was extracted with chloroform. The extract obtained was washed with water, dried over anhydrous magnesium sulfate, and then the solvent was distilled off under reduced pressure. The residue formed was dissolved in 20 ml. off trifluoroacetic acid under ice-cooling and 20 ml. of water was immediately added to the solution followed by stirring for 15 minutes at 5°-10° C. The reaction mixture was neutralized with sodium hydrogencarbonate and extracted with chloroform. The extract was washed with water, dried over anhydrous magnesium sulfate, and then the solvent was distilled off under reduced pressure. Thereafter, the residue formed was subjected to a silica gel column chromatography (diameter 3 cm., height 7 cm.) and from the fraction recovered therefrom using a 8 : 2 mixture of chloroform and methanol 820 mg. of sticky 2-(1-hydroxy-1-methyl-4-indanyloxymethyl)morpholine was obtained.

Elemental analysis for $C_{15}H_{21}NO_3$:

| | C | H | N |
|---|---|---|---|
| Calculated: | 68.41% | 8.04% | 5.32% |
| Found: | 68.25% | 8.31% | 5.28% |

Nuclear magnetic resonance spectra ($CDCl_3$, ppm.): 1.54 (s, 3H, —$CH_3$), 6.50-7.33 (m, 3H, phenyl proton).

(b). In 20 ml. of anhydrous toluene was dissolved 100 mg. of 2-(1-hydroxy-1-methyl-4-indanyloxymethyl)-morpholine and after adding thereto 10 mg. of p-toluenesulfonic acid monohydrate, the mixture was refluxed for 4 hours. After cooling, the reaction mixture was washed successively with aqueous 3% sodium hydrogencarbonate solution and water, dried over anhydrous magnesium sulfate, and then the solvent was distilled off under reduced pressure. The residue formed was subjected to a silica gel column chromatography (diameter 1.5 cm., height 7 cm.) and from the fraction recovered therefrom using a 98 : 2 mixture of chloroform and methanol as an eluting solution, 69 mg. (yield 74.5%) of sticky 2-(3-methyl-7-indenyloxymethyl)morpholine was obtained. The oxalate of the product had a melting point of 151°-152° C.

Elemental analysis for $C_{15}H_{19}NO_2$:

| | C | H | N |
|---|---|---|---|
| Calculated: | 73.44% | 7.81% | 5.71% |
| Found: | 73.10% | 7.74% | 5.62% |

Nuclear magnetic resonance spectra ($CDCl_3$, ppm.): 2.12 (m, 3H,

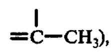

6.17 (s, 1H, =CH—), 6.60-7.36 (m, 3H, phenyl proton).

EXAMPLE 12

In 40 ml. of dimethyl sulfoxide were dissolved 2.9 g. (0.0156 mole) of the potassium salt of 1-oxo-4-indanol and 4.7 g. (0.015 mole) of 4-isopropyl-2-p-toluenesulfonyloxymethyl morpholine and the solution was stirred for 15 hours at 100°-110° C. After cooling the reaction mixture, dimethylsulfoxide was distilled off under reduced pressure and the residue formed was mixed with 50 ml. of dichloromethane. The mixture was then washed successively with 30 ml. of water, 30 ml. of aqueous 5% sodium hydroxide solution, and 30 ml. of water. The organic layer formed was recovered, dried over anhydrous magnesium sulfate, and the solvent was distilled off under reduced pressure to provide an oily residue. The residue was dissolved in a small amount of ethyl acetate and the solution was subjected to a silica gel chromatography (column diameter 1.5 cm., height 20 cm.) and fractions were collected (using ethyl acetate as an eluting solution) and concentrated to provide 2.5 g. of 4-isopropyl-2-(1-oxo-4-indanyloxymethyl)morpholine.

Elemental analysis for $C_{17}H_{23}NO_3$:

| | C | H | N |
|---|---|---|---|
| Calculated: | 70.56% | 8.01% | 4.84% |
| Found: | 70.19% | 7.98% | 4.55% |

Nuclear magnetic resonance spectra ($CDCl_3$, ppm.):

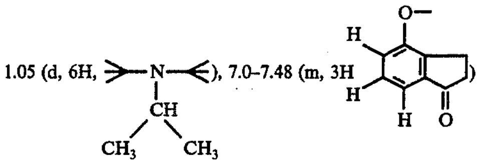

By following the similar procedure as above using 2.9 g. of the potassium salt of 3-oxo-4-indanol, 1.05 g. of 4-isopropyl-2-(3-oxo-4-indanyloxymethyl)morpholine was obtained.

| | C | H | N |
|---|---|---|---|
| Calculated: | 70.56% | 8.01% | 4.84% |
| Found: | 70.31% | 8.00% | 4.63% |

Nuclear magnetic resonance spectra ($CDCl_3$, ppm.):

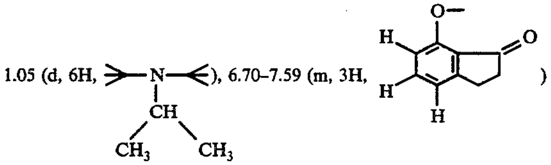

(b). A solution of 1.2 g. (0.004 mole) of 4-isopropyl-2-(1-oxo-4-indanyloxymethyl)morpholine in 5 ml. of anhydrous tetrahydrofuran was added gradually under ice-cooling in a nitrgen gas stream to a solution of a Grignard reagent prepared from 0.41 g. (0.017 atom) of magnesium and methyl bromide using 30 ml. of anhydrous tetrahydrofuran as a solvent and thereafter the mixture was stirred for 2 hours at room temperature. Then, to the reaction mixture was added ice water and the product was extracted thrice each with 30 ml. of methylene chloride. The organic layer was recovered, washed with water, and dried over anhydrous magnesium sulfate. Then, the solvent was distilled off under reduced pressure and the residue formed was subjected to a silica gel column chromatography (column diameter 1.5 cm., height 20 cm.), whereby 1.1 g. of 2-(1-hydroxy-1-methyl-4-indanyloxymethyl)-4-isopropyl morpholine was obtained.

Elemental analysis for $C_{18}H_{27}NO_3$:

| | C | H | N |
|---|---|---|---|
| Calculated: | 70.79% | 8.91% | 4.59% |
| Found: | 70.58% | 8.83% | 4.31% |

Nuclear magnetic resonance spectra ($CDCl_3$, ppm.):

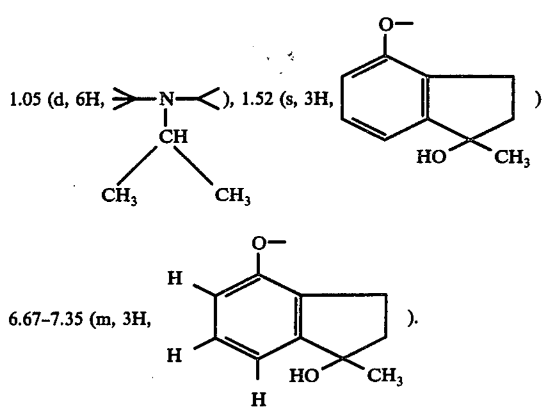

By following the similar procedure as above using 1.2 g. of 2-(1-oxo-7-indanyloxymethyl)-4-isopropyl morpholine, 1.1 g. of 2-(1-hydroxy-1-methyl-7-indanyloxymethyl)-4-isopropyl morpholine was obtained.

Elemental analysis for $C_{18}H_{27}NO_3$:

| | C | H | N |
|---|---|---|---|
| Calculated: | 70.79% | 8.91% | 4.59% |
| Found: | 70.70% | 8.89% | 4.46% |

Nuclear magnetic resonance spectra ($CDCl_3$, ppm.):

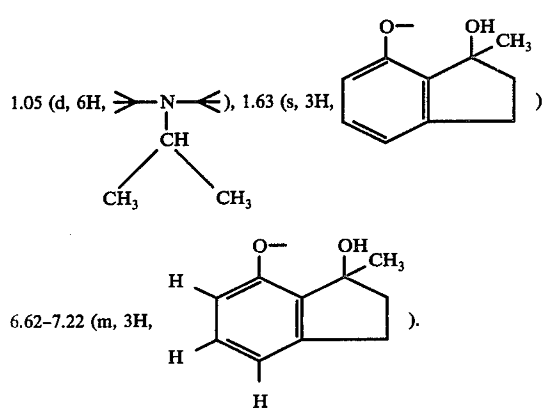

(c). In 50 ml. of toluene was dissolved 2.9 g. (0.0095 mole) of 2-(1-hydroxy-1-methyl-4-indanyloxymethyl)-4-isopropyl morpholine and after adding to the solution 0.1 g. of p-toluenesulfonic acid as a catalyst, the mixture was refluxed for 5 hours. After cooling, the reaction mixture was washed successively with aqueous 5% sodium hydrogencarbonate and water and dried over anhydrous magnesium sulfate. The solvent was distilled off under reduced pressure and the residue formed was subjected to a silica gel column chromatography (column diameter 1.5 cm., height 20 cm.) to provide 2.6 g. of 4-isopropyl-2-(3-methyl-7-indenyloxymethyl)morpholine. The citrate of the product had a melting point of 101°-103° C. (recrystallized from methanol).

Elemental analysis for $C_{18}H_{25}NO_2.C_6H_8O_7$:

| | C | H | N |
|---|---|---|---|
| Calculated: | 60.11% | 6.94% | 2.92% |
| Found: | 59.74% | 7.00% | 2.58% |

Nuclear magnetic resonance spectra of the free base ($CDCl_3$, ppm):

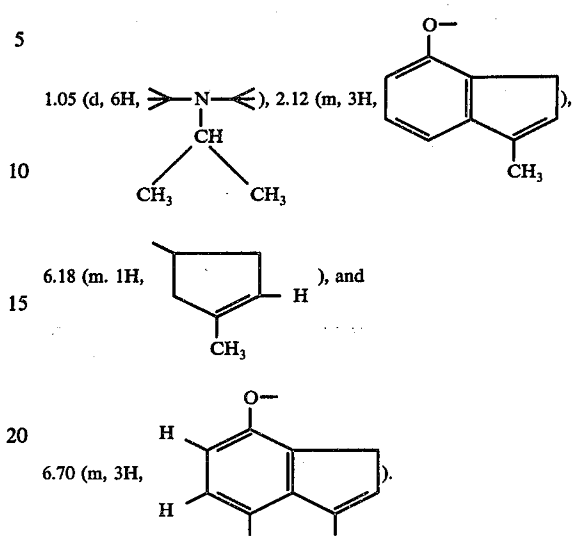

By following the same procedure as above using 2-(3-hydroxy-3-methyl-4-indanyloxymethyl)-4-isopropyl morpholine, 4-isopropyl-2-(3-methyl-4-indenyloxymethyl)morpholine was produced. The citrate of the product had a melting point of 114°-116° C. (recrystallized from methanol).

Elemental anlysis for $C_{18}H_{25}NO_2.C_6H_8O_7$:

| | C | H | N |
|---|---|---|---|
| Calculated: | 60.11% | 6.94% | 2.92% |
| Found: | 59.82% | 7.04% | 2.65% |

Nuclear magnetic resonance spectra as the free base ($CDCl_3$, ppm):

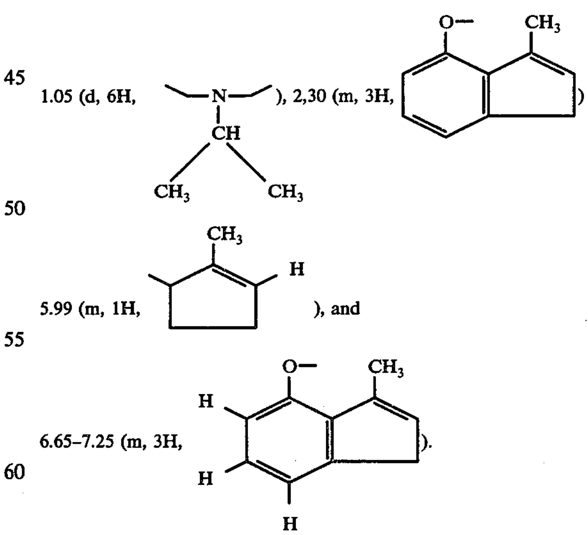

EXAMPLE 13

(a). To a mixture of 16.2 g. of 3-methyl-1-oxo-5-indanol, 8 g. of sodium hydroxide, and 100 ml. of water was added 50 ml. of 1-chloro-2,3-epoxypropane and after stirring vigorously for 16 hours at room temperature, the reaction mixture was extracted with 300 ml. of benzene. The extract was washed twice each with 100 ml. of water and then the extract was subjected to a vacuum distillation to remove benzene and excessive 1-chloro-2,3-epoxypropane. Thereafter, 50 ml. of isopropylamine and 100 ml. of methanol were added to the residue followed by stirring for 18 hours at room temperature and excessive isopropylamine and methanol were distilled off under reduced pressure. Then, about 50 ml. of acetone was added to the residue, whereby crystals precipitated. After allowing to stand overnight the system, the crysltas were recovered by filtration to provide 15.2 g. (yield 54.8%) of 3-isopropylamino-1-(3-methyl-1-oxo-5-indanyloxy)-2-propanol. Furthermore, by recrystallizing the product from acetone, the white crystal of the product melting at 113°-114° C. was obtained.

Elemental analysis for $C_{16}H_{23}NO_3$:

| | C | H | N |
|---|---|---|---|
| Calculated: | 69.28% | 8.36% | 5.05% |
| Found: | 69.14% | 8.29% | 5.12% |

(b). To a mixture of 2.77 g. of 3-isopropylamino-1-(3-methyl-1-oxo-5-indanyloxy)-2-propanol, 50 ml. of methylene chloride, and 1.2 g. of triethylamine was added dropwise 2.1 g. of bromoacetyl bromide with stirring under ice-cooling and the mixture was stirred for 18 hours at room temperature. Thereafter, methylene chloride was distilled off and after adding to the residue formed 50 ml. of benzene and 50 ml. of water to form a solution, the benzene layer formed was recovered, washed with 20 ml. of aqueous 5% hydrochloric acid solution and then twice each with 30 ml. of water, dried over anhydrous magnesium sulfate. Then, benzene was distilled off from the reaction mixture and after adding to the residue a solution of 0.3 g. of metallic sodium in 50 ml. of methanol, the mixture was refluxed for 3 hours. Methanol was distilled off and then to the residue were added 50 ml. of benzene and 30 ml. of water. The benzene layer formed was recovered from the mixture, washed twice with 20 ml. of aqueous 5% hydrochloric acid solution and then 20 ml. of water, and dried over anhydrous magnesium sulfate. Then, benzene was distilled off and 2 ml. of acetone was added to the residue to form precipitates, which were recovered by filtration. Thus, 2.3 g. (yield 73.6%) of 4-isopropyl-2-(3-methyl-1-oxo-5-indanyloxymethyl)-5-oxomorpholine was obtained. By recrystallizing the product from acetone, the faint yellow crystals of the product melting 150°-152° C. were obtained.

Elemental analysis for $C_{18}H_{23}NO_4$:

| | C | H | N |
|---|---|---|---|
| Calculated: | 68.12% | 7.31% | 4.41% |
| Found: | 68.21% | 7.23% | 4.31% |

(c). In 10 ml. of tetrahydrofuran was dissolved 3.17 g. of 4-isopropyl-2-(3-methyl-1-oxo-5-indanyloxymethyl)-5-oxomorpholine and the solution was added dropwise to the suspension of 0.4 g. of lithium aluminum hydride in 20 ml. of tetrahydrofuran followed by stirring for 5 hours at room temperature. Thereafter, 0.4 ml. of water, 0.4 ml. of aqueous 15% sodium hydroxide solution, and then 1.2 ml. of water were added successively to the mixture followed by stirring for 30 minutes and then the filtrate obtained was concentrated under reduced pressure to provide 2.1 g. (yield 68.8%) of 2-(1-hydroxy-3-methyl-5-indanyloxymethyl)-4-isopropylmorpholine having a boiling point of 174°-178° C./0.5 mm.Hg was obtained.

Elemental analysis for $C_{18}H_{27}NO_3$:

| | C | H | N |
|---|---|---|---|
| Calculated: | 70.79% | 8.91% | 4.59% |
| Found: | 70.63% | 8.96% | 4.55% |

(d). A mixture of 3.05 g. of 2-(1-hydroxy-3-methyl-5-indanyloxymethyl)-4-isopropylmorpholine, 0.3 g. of p-toluenesulofnic acid, and 50 ml. of xylene was refluxed with stirring for 36 hours and then xylene was distilled off under reduced pressure. The residue formed was adsorbed on 20 g. of silica gel filled in a column, the residue adsorbed was eluted with 100 ml. of chloroform and then 100 ml. of ethyl acetate as the eluents, and the ethyl acetate eluate thus collected was dried to provide 1.5 g. (yield 52.2%) of colorless and oily 4-isopropyl-2-(3-methyl-5-indenyloxymethyl)morpholine. The citrate of the product had a melting point of 126°-128° C.

Elemental analysis for $C_{18}H_{25}NO_2$:

| | C | H | N |
|---|---|---|---|
| Calculated: | 75.22% | 8.77% | 4.87% |
| Found: | 75.12% | 8.53% | 4.98% |

EXAMPLE 14

(a). By following the similar procedure as in Example 13-(a), 3-isopropylamino-1-(3-methyl-1-oxo-5-indanyloxy)-2-propanol was prepared.

(b). Also, by following the similar procedure as in Example 13-(b) using the above product, 4-isopropylamino-2-(3-methyl-1-oxo-5-indanyloxymethyl)-5-oxomorpholine was prepared.

(c). A solution of 2.7 g. of phenylmagnesium bromide in 30 ml. of tetrahydrofuran was added dropwise to a mixture of 3.17 g, of 4-isopropyl-2-(3-methyl-1-oxo-5-indanyloxymethyl)-5-oxomorpholine and 200 ml. of tetrahydrofuran with stirring at room temperature and the mixture was further stirred for 30 minutes. Then, adding a small amount of water to the reaction mixture, tetrahydrofuran was distilled off from the reaction mixture under reduced pressure. To the residue formed were added 100 ml. of ethyl acetate and 100 ml. of water to dissolve the residue therein and the ethyl acetate layer formed was recovered and washed twice each with 50 ml. of water and then with 50 ml. of saturated sodium chloride aqueous solution. Then, ethyl acetate was distilled off and the residue formed was adsobed on a silica gel column prepared from 150 ml of silica gel. in chloroform. The residue adsorbed was then eluted with ethyl acetate and after removing the first 10 ml. of the ethyl acetate eluate emerging from the column, 300 ml. of the ethyl acetate eluate thereafter was collected and dried to provide 3.25 g. (yield 82.3%) of oily 2-(1-hydroxy-3-methyl-1-phenyl-5-indanyloxymethyl)-4-isopropyl-5-oxomorpholine.

Elemental analysis for $C_{24}H_{29}NO_4$:

| | C | H | N |
|---|---|---|---|
| Calculated: | 72.88% | 7.39% | 3.54% |

-continued

| | C | H | N |
|---|---|---|---|
| Found: | 72.83% | 7.21% | 3.44% |

(d). After mixing 2.5 g. of 2-(1-hydroxy-3-methyl-1-phenyl-5-indanyloxymethyl)-4-isopropyl-5-oxomorpholine, 100 ml. of tetrahydrofuran, and 1.0 g. of lithium aluminum hydride under ice-cooling, the mixture was stirred for 18 hours at room temperature and then 1 ml. of water, 1 ml. of 15% sodium hydroxide aqueous solution, and then 3 ml. of water were added to the mixture followed by stirring for 30 minutes. The mixture was then filtered and the filtrate recovered was dried under reduced pressure. The residue formed was adsorbed on a silica gel column prepared from 50 ml. of silica gel in chloroform and then eluted using ethyl acetate as the eluent. After removing the first 5 ml. of the ethyl acetate eluate emerging from the column, 150 ml. of the subsequent ethyl acetate eluate was collected and dried to provide 2.0 g. (yield 83.0%) of 2-(1-hydroxy-3-methyl-1-phenyl-5-indanyloxymethyl)-4-isopropylmorpholine.

Elemental analysis for $C_{24}H_{31}NO_3$:

| | C | H | N |
|---|---|---|---|
| Calculated: | 75.56% | 8.19% | 3.67% |
| Found: | 75.60% | 8.13% | 3.64% |

(e). In 50 ml. of xylene was dissolved 1.5 g. of 2-(1-hydroxy-3-methyl-1-phenyl-5-indanyloxymethyl)-4-isopropylmorpholine and after adding to the solution 5 mg. of p-toluenesulfonic acid, the mixture was refluxed for 3 hours. Then, xylene was distilled off and the residue formed was adsorbed on a silica gel column prepared from 100 ml. of silica gel in chloroform and eluted with ethyl acetate. After removing the first 10 ml. of the ethyl acetate eluate emerging from the column, 200 ml. of the subsequent ethyl acetate eluate was collected and dried to provide 0.9 g. (yield 62.7%) of 4-isopropyl-2-(1-methyl-3-phenyl-6-indenyloxymethyl)morpholine. The citrate of the product had a melting point of 111°-112.5° C.

Elemental analysis for $C_{24}H_{29}NO_2$:

| | C | H | N |
|---|---|---|---|
| Calculated: | 79.30% | 8.04% | 3.85% |
| Found: | 79.12% | 8.12% | 3.93% |

EXAMPLE 15

To a mixture of 14.8 g. of 1-oxo-5-indanol, 8 g. of sodium hydroxide, and 100 ml. of water was added 50 ml. of 1-chloro-2,3-epoxypropane and after stirring vigorously the mixture for 16 hours at room temperature, 300 ml. of benzene and 100 ml. of water were added to the mixture. Then, the benzene layer fomred was recovered, washed twice each with 100 ml. of water, and then subjected to a distillation under reduced pressure to distill off benzene and then excessive 1-chloro-2,3-epoxypropane. The residue formed was mixed with 50 ml. of isopropylamine and 100 ml. of methanol and after stirring the mixture for 18 hours at room temperature, excessive isoporpylamine and methanol were distilled off under reduced pressure. Then, to the residue formed was added about 50 ml. of acetone and the mixture was allowed to stand overnight in a cold chamber to form crystals, which were recovered by filtration to provide 13.4 g. (yield 51%) of 3-isopropylamino-1-(1-oxo-5-indanyloxy)-2-propanol. By recrystallizing the product from acetone, the colorless crystals thereof melting at 100°-102° C. was obtained.

Elemental analysis for $C_{15}H_{21}NO_3$:

| | C | H | N |
|---|---|---|---|
| Calculated: | 68.41% | 8.04% | 5.32% |
| Found: | 68.51% | 8.12% | 5.23% |

(b). After adding dropwise 2.1 g. of bromoacetyl bromide to a mixture of 2.63 g. of 3-isopropylamino-1-(1-oxo-5-indanyloxy)-2-propanol, 50 ml. of methylene chloride, and 1.2 g. of triethylamine with stirring under ice-cooling, the mixture was stirred for 18 hours at room temperature and then methylene chloride was distilled off. To the residue formed were added 50 ml. of benzene and 50 ml. of water to dissolve the residue and then the benzene layer was separated from the system, washed twice each with 30 ml. of water, and dried over anhydrous magnesium sulfate. Then, benzene was distilled off and then 50 ml. of methanol having dissolved therein 0.3 g. of metallic sodium was added to the residue followed by reflux for 3 hours. Then, methanol was distilled off and to the residue were added 50 ml. of benzene and 30 ml. of water to dissolve the residue. The benzene layer formed was recovered, washed twice each with 20 ml. of water, and adsorbed on a silica gel column prepared from 50 ml. of silica gel in 100 ml. of chloroform. The residue was then eluted using ethyl acetate as the eluent and after removing the first 50 ml. of the ethyl acetate eluate emerging from the column, 100 ml. of the subsequent ethyl acetate eluate was collected and dried to provide 2.1 g. (yield 69.2%) of 4-isopropyl-5-oxo-2-(1-oxo-5-indanyloxymethyl)morpholine.

Elemental analysis for $C_{17}H_{21}NO_4$:

| | C | H | N |
|---|---|---|---|
| Calculated | 67.31% | 6.98% | 4.62% |
| Found: | 67.15% | 6.95% | 4.53% |

(c). A solution of 2.7 g. of phenylmagnesium bromide in 20 ml. of tetrahydrofuran was added dropwise to a mixture of 3.03g. of 4-isopropyl-5-oxo-2-(1-oxo-5-indanyloxymethyl)morpholine in 100 ml of tetrahydrofuran with stirring at room temperature and the mixture thus obtained was stirred for 30 minutes. Then, after adding to the mixture a small amount of water, tetrahydrofuran was distilled off under reduced pressure. To the residue formed were added 100 ml. of ethyl acetate and 100 ml. of water to dissolve the residue and the ethyl acetate layer formed was recovered, washed twice each with 50 ml. of water and then 50 ml. of saturated aqueous sodium chloride aqueous solution, and then ethyl acetate was distilled off. The residue formed was adsorbed on a silica gel column prepared from 150 ml. of silica gel in chloroform and then eluted with ethyl acetate. After removing the first 10 ml. of the ethyl acetate eluate emerging from the column, 300 ml. of the subsequent ethyl acetate eluate was collected and dried to provide 2.93 g. (yield 77%) of oily 2-(1-hydroxy-1-phenyl-5-indanyloxymethyl)-4-isopropyl-5-oxomorpholine.

Elemental analysis for $C_{23}H_{27}NO_4$:

| | C | H | N |
|---|---|---|---|
| Calculated: | 72.42% | 7.13% | 3.67% |
| Found: | 72.19% | 6.95% | 3.71% |

(d). After mixing 2.5 g. of 2-(1-hydroxy-1-phenyl-5-indanyloxymethyl)-4 -isopropyl-5-oxomorpholine, 100 ml. of tetrahydrofuran, and 1.0 g. of lithium aluminum hydride under ice-cooling, the mixture was stirred for 18 hours at room temperature and then 1 ml. of water, 1 ml. of aqueous 15% sodium hydroxide aqueous solution, and then 3 ml. of water were added to the mixture followed by stirring for 30 minutes. The mixture thus obtained was filtered and the filtrate was distilled and the residue formed was adsorbed on a silica gel column prepared from 50 ml. of silica gel in chloroform and eluted with ethyl acetate. After removing the first 5 ml. of the ethyl acetate eluate, 200 ml. of the subsequent ethyl acetate eluate was collected and dried to provide 2.05 g. (yield 85.3%) of 2-(1-hydroxy-1-phenyl-5-indanyloxymethyl)-4-isopropylmorpholine.

Elemental analysis for $C_{23}H_{29}NO_3$:

| | C | H | N |
|---|---|---|---|
| Calculated: | 75.17% | 7.95% | 3.81% |
| Found: | 74.96% | 7.81% | 3.79% |

(e). In 50 ml. of xylene was dissolved 1.5 g. of 2-(1-hydroxy-1-phenyl-5-indanyloxymethyl)-4-isopropylmorpholine and after adding to the solution 5 mg. of p-toluenesulfonic acid, the mixture was refluxed for 8 hours. Thereafter, xylene was distilled off under reduced pressure and the residue was adsorbed on a silica gel column prepared from 100 ml. of silica gel in chloroform and eluted using ethyl acetate as the eluent. After removing the first 10 ml. of the ethyl acetate eluate emerging from the column, 200 ml. of the subsequent ethyl acetate eluate was collected and dried to provide 1.0 g. (yield 70.2%) of 4isopropyl-2-(3-phenyl-6-indenyloxymethyl)morpholine. The citrate of the product had a melting point of 107°-109° C.

Elemental analysis for $C_{23}H_{27}NO_2$:

| | C | H | N |
|---|---|---|---|
| Calculated: | 79.05% | 7.79% | 4.01% |
| Found: | 78.96% | 7.83% | 3.90% |

EXAMPLE 16

(a) After mixing 3.03 g, of 4-isopropyl-5-oxo-2-(1-oxo-5-indanyloxymethyl)morpholine, 100 ml. of tetrahydrofuran, and 2.0 g. of lithium aluminum hydride under ice-cooling, the mixture was stirred for 18 hours at room temperature. Then, 2.0 ml. of water, 2.0 ml. of 15% sodium hydroxide aqueous solution, and then 6 ml. of water were added to the mixture followed by stirring for 30 minutes. The mixture was then filtered and the filtrate was concentrated. The residue formed was adsorbed on a silica gel column prepared from 100 ml. of silica gel in chloroform and then eluted with ethyl acetate as the eluent. After removing the first 20 ml. of the ethyl acetate eluate emerging from the column, 300 ml. of the subsequent ethyl acetate eluate was collected and dried to provide 2.0 g. (yield 68.7%) of oily 2-(1-hydroxy-5-indanyloxymethyl)-4-isopropylmorpholine.

Elemental analysis for $C_{17}H_{25}NO_3$:

| | C | H | N |
|---|---|---|---|
| Calculated: | 70.07% | 8.65% | 4.81% |
| Found: | 69.96% | 8.52% | 4.80% |

(b) A mixture of 2.91 g. of oily 2-(1-hydroxy-5-indanyloxymethyl)-4-isopropylmorpholine, 100 ml. of xylene, and 20 mg. of p-toluenesulfonic acid was refluxed with stirring for 4 hours and then xylene was distilled off from the reaction mixture. Then, the residue formed was adsorbed on a silica gel column prepared from of 100 ml. of silica gel in chloroform and eluted using ethyl acetate as the eluent. After removing the first 20 ml. of the ethyl acetate eluate emerging from the column, 200 ml. of the subsequent ethyl acetate eluting solution was collected and dried to provide 1.5 g. (yield 55%) of a mixture of oily 2-(6-indenyloxymethyl)-4-isopropylmorpholine and 2-(5-indenyloxymethyl)-4-isopropylmorpholine. The citrate of the product had a melting point of 146.5°-148° C.

| | C | H | N |
|---|---|---|---|
| Calculated: | 74.69% | 8.48% | 5.12% |
| Found: | 74.42% | 8.53% | 5.20% |

EXAMPLE 17

(a). After adding dropwise a solution of 5 g. of methyl magnesium bromide in 27 ml. of tetrahydrofuran to a mixture of 4.0 g. of 4-isopropyl-5-oxo-2-(1-oxo-5-indanyloxymethyl)morpholine and 100 ml. of tetrahydrofuran with stirring at room temperature, the mixture was stirred for 3 hours at room temperature. Then, after adding a small amount of water to the reaction mixture, the solvent was distilled off under reduced pressure. To the residue formed were added 50 ml. of ethyl acetate and 50 ml. of water to dissolve the residue and they were filtered. The ethyl acetate filtrate (100 ml.) was recovered, washed twice each with 50 ml. of saturated sodium chloride aqueous solution, and condensed under reduced pressure, the obtained residue was adsorbed on a silica gel column prepared from 100 ml. of silica gel in chloroform, and then eluted using ethyl acetate as the eluting solution. After removing the first 30 ml. of the ethyl acetate eluting solution emerging from the column, 300 ml. of the subsequent ethyl acetate eluting solution was collected and dried to provide 2.5 g. (yield 59.3%) of oily 2-(1-hydroxy-1-methyl-5-indanyloxymethyl)-4-isopropyl-5-oxomorpholine.

Elemental analysis for $C_{18}H_{25}NO_4$:

| | C | H | N |
|---|---|---|---|
| Calculated: | 67.69% | 7.89% | 4.39% |
| Found: | 67.53% | 7.78% | 4.35% |

(b) After mixing 3.19 g. of oily 2-(1-hydroxy-1-methyl-5-indanyloxymethyl)-4-isopropyl-5-oxomorpholine, 100 ml. of tetrahydrofuran, and 1.5 g. of lithium aluminum hydride under ice-cooling, the mixture was stirred for 18 hours at room temperature and to the mixture were added 1.5 ml. of water, 1.5 ml. of 15% sodium hydroxide aqueous solution, and then 4.5 ml. of water followed by stirring for 30 minutes. The mixture was then filtered and the filtrate was concentrated under reduced pressure, adsorbed on a silica gel column prepared from 70 ml. of silica gel in chloroform, and then eluted using ethyl acetate as the eluting solution. After removing then first 20 ml. of the ethyl acetate eluting solution emerging from the column, 200 ml. of the subsequent ethyl acetate eluting solution was collected and dried to provide 2.3 g. (yield 75.4%) of oily 2-(1-hydroxy-1-methyl-5-indanyloxymethyl)-4-ispropylmorpholine.

Elemental analysis for $C_{18}H_{27}NO_3$:

| | C | H | N |
|---|---|---|---|
| Calculated: | 70.79% | 8.91% | 4.59% |
| Found: | 70.83% | 9.00% | 4.61% |

(c) A mixture of 3.05 g. of oily 2-(1-hydroxy-1-methyl-5-indanyloxymethyl)-4-isopropylmorpholine, 100 ml. of xylene, and 20 mg. of p-toluenesulfonic acid was refluxed with stirring for 4 hours and then the solvent was distilled off. Then, the residue formed was adsorbed on a silica gel column prepared from 100 ml. of silica gel in chloroform and eluted with ethyl acetate. After removing the first 10 ml. of the ethyl acetate eluate emerging from the column, 200 ml. of the subsequent ethyl acetate eluate was collected and concentrated under reduced pressure to provide 2.1 g. (yield 73.3%) of 4-isopropyl-2-(3-methyl-6-indenyloxymethyl)morpholine. The citrate of the product had a melting point of 159°-161° C.

Elemental analysis for $C_{18}H_{25}NO_2$:

| | C | H | N |
|---|---|---|---|
| Calculated: | 75.22% | 8.77% | 4.87% |
| Found: | 75.31% | 8.73% | 4.84% |

EXAMPLE 18

Tablet composition:
1 tablet contains

| | |
|---|---|
| 2-(7-Indenyloxymethyl)-4-isopropyl morpholine citrate | 25 mg. |
| lactose | 70 mg. |
| starch | 25 |
| talc | 4 |
| magnesium stearate | 1 |

The above ingredients are mixed, granulated and compressed into tablets according to conventional method. Weight of one tablet is 125 mg.

EXAMPLE 19 a. In a mixed solution of 29 ml. of 70% sodium hydroxide solution and 35 g. of 2-aminoethyl hydrogen sulfate ($H_2N$-$CH_2CH_2OSO_3H$) was added 9.4 g. of 1-(7-indenyloxy)-2,3-epoxypropane (containing about 35% 1-(4-indenyloxy)-2,3-epoxypropane) dissolved in 50 ml. of methanol and the mixture was stirred for one hour at 55° C. To the mixture was added 50 ml. of 70% sodium hydroxide and stirred for a further 16 hours at 55° C. After cooling, 300 ml. of water was added to the reaction mixture and then the product was extracted three times each time with 100 ml. of toluene. The extracts were combined, washed with water, dried, and then the residue was distilled. By collecting the fractions having boiling points of 146°-156° C/0.5 mm Hg., 6.7 g (yield 58.0%) of oily 2-(7-indenyloxymethyl(morpholine (containing 32% 2-(4-indenyloxymethyl) morpholine was obtained.

The proportions of the both isomers was measured by gas chromatography after trifluoroacetylating the isomer mixture with trifluoroacetic anhydride.

Elemental analysis for $C_{14}H_{17}NO_2$:

| | C(%) | H(%) | N(%) |
|---|---|---|---|
| Calculated: | 72.70 | 7.41 | 6.06 |
| Found: | 72.91 | 7.50 | 5.95 |

b. In 30 ml. of acetone was dissolved 3 g. of the oily base obtained in procedure a, supra and after acidifying the solution thus obtained with isopropanol-hydrochloric acid, the solution was mixed with 50 ml. of ether. The mixture was allowed to stand overnight in an ice chamber at −10° C. to precipitate crystals, which were recovered by filtration to provide 2.8 g. (yield 80.4%) of 2-(7-indenyloxymethyl)morpholine hydrochloride (containing 40% 2-(4-indenyloxymethyl)morpholine hydrochloride) melting at 143°-155° C.

The proportions of the both isomers in the product was measured by gas chromatography after trifluoroacetylating the product with trifluoroacetic anhydride.

Elemental analysis for $C_{14}H_{18}NO_2Cl$:

| | C(%) | H(%) | N(%) | Cl(%) |
|---|---|---|---|---|
| Calculated: | 62.80 | 6.78 | 5.23 | 13.24 |
| Found: | 62.84 | 6.81 | 5.24 | 13.01 |

c. In 70 ml. of acetone was dissolved 3 g. of the oily base obtained in the procedure a), the solution was weakly acidified by isopropanol-hydrochloric acid under ice-cooling and then allowed to stand overnight in a refrigerator. The crystals thus precipitated were recovered by filtration and washed with acetone and then ether to provide 1.1 g. of 2-(4-indenyloxymethyl)-morpholine hydrochloride (containing 15% 2-(7-indenyloxymethyl)-morpholine hydrochloride) showing melting point of 159°-163° C. Then, by repeating the recrystallization from methanol, pure 2-(4-indenyloxymethyl)morpholine hydrochloride showing melting point of 175°-176° C. was obtained.

Elemental analysis for $C_{14}H_{18}NO_2Cl$:

| | N(%) |
|---|---|
| Calculated: | 5.23 |
| Found: | 5.31 |

Nuclear magnetic resonance spectra: $CDCl_3$ + $D_6$-DMSO; ppm)

3.0-3.4 (4H, m, 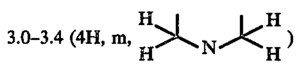 )

4.0-4.1 (4H, m, —O—$CH_2$—, 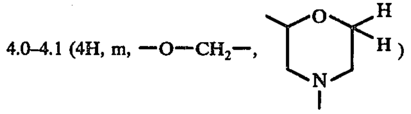 )

-continued 4.3 (1H, m, )

3.4 (2H, )

6.5 (1H, doublet, , J = 6Hz)

7.0 (1H, doublet, , J = 6Hz)

6.8 (1H, q, )

7.1 (2H, d, )

9.5 (2H, $\overset{+}{N}H_2Cl^-$ ).

The mother liquor and washings were combined, dried up under reduced pressure, and after adding thereto 50 ml. of toluene followed by drying again under reduced pressure, the residue obtained was dissolved once in 30 ml. of acetone. The solution thus obtained was allowed to stand overnight at room temperature and the crystals thus formed were recovered by filtration and washed with acetone to provide 1.7 g. of 2-(7-indenyloxymethyl)morpholine hydrochloride(-containing 10% 4-indenyloxy isomer) showing a melting point of 138°-153° C. The proportions of the both isomers was measured by gas chromaotography after trifluoroacetylating the product with trifluoroacetic anhydride. Then, by repeating the recrystallization from methanol, 1.7 g. of pure 2-(7-indenyloxymethyl)-morpholine hydrochloride having the following properties was obtained.

Elemental analysis for $C_{14}H_{18}NO_2Cl$:

| | N(%) |
|---|---|
| Calculated: | 5.23 |
| Found: | 5.29 |

Nuclear magnetic resonance spectra:

($CDCl_3$ + $D_6$-DMSO: ppm):

3.0-3.4 (4H, m, )

-continued 4.0-4.2 (4H, m —O—$CH_2$—, )

4.3 (1H, m, )

3.34 (2H, )

6.58 (1H, doublet, , J = 6 Hz)

6.84 (1H, doublet , J = 6 Hz)

6.78 (1H, d, )

7.04 (1H, d, )

7.20 (1H, t, )

10.0 (2H, $\overset{+}{N}H_2$ $Cl^-$)

EXAMPLE 20

To a mixture of 6 g. of 20% sodium hydroxide solution and 3.8g. of 2-aminoethyl hydrogen sulfate was added 2.0 g. of 1-(1-hydroxy-4-indanyloxy)-2,3-epoxy-propane dissolved in 10 ml. of ethanol and the mixture was stirred for 1 hour at 60° C. To the solution was added 2.0 g. of 20% sodium hydroxide solution and the mixture was further stirred for 16 hours at 60° C. After cooling, 50 ml. of water was added to the mixture and the reaction was extracted three times each time with 20 ml. of toluene. The extracts were combined, washed with water, dried with anhydrous sodium sulfate, and then the solvent was distilled off from the mixture under reduced pressure. Then, the residue was subjected to silica gel column chromatography and eluted with chloroformmethanol (9 : 1 by volume ratio) to provide 900 mg. of 2-(1-hydroxy-4-indanyloxymethyl)-morpholine having a melting point of 115°-117° C.

Elemental analysis for $C_{14}H_{19}NO_3$:

| | C(%) | H(%) | N(%) |
|---|---|---|---|
| Calculated: | 67.45 | 7.68 | 5.62 |
| Found: | 67.01 | 7.66 | 5.43 |

Nuclear magnetic resonance spectra:

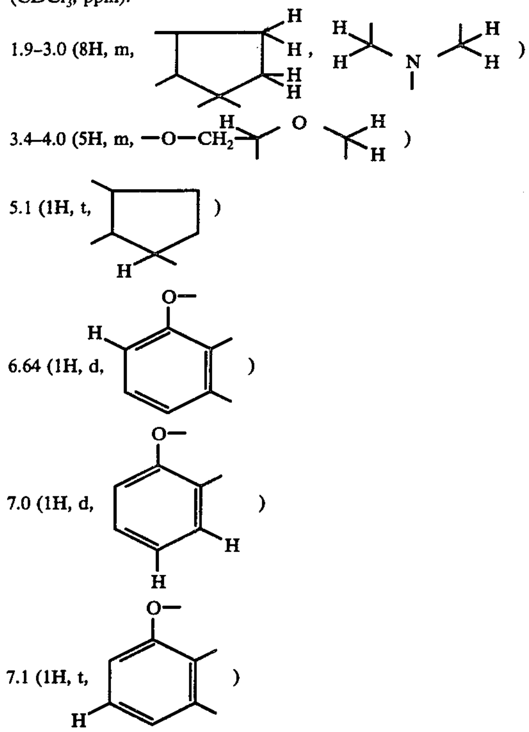

-continued

EXAMPLE 21

To a mixed solution of 6 g. of 20% sodium hydroxide solution and 3.8 g. of 2-aminoethyl hydrogen sulfate was added 2.0 g. of 1-(1-oxo-4-indanyloxy)-2,3-epoxypropane dissolved in 10 ml. of ethanol and the mixture was stirred for 1 hour at 60° C. Then, 20 g. of 20% sodium hydroxide solution was added to the mixture and the resultant mixture was further stirred for 16 hours at 60° C. After cooling, 50 ml. of water was added to the mixture and the reaction mixture was extracted with 20 ml. of toluene. The extract was washed with water, dried over anhydrous sodium sulfate, and then the solvent was distilled away under reduced pressure. The residue formed was subjected to silica gel column chromatography and eluted by a solvent mixture of chloroform-methanol (98 : 2 by volume ratio) to obtain 110 mg. of oily 2-(1-oxo-4-indanyloxymethyl)-morpholine from the eluate.

Elemental analysis for $C_{14}H_{17}NO_3$:

| | C(%) | H(%) | N(%) |
|---|---|---|---|
| Calculated: | 67.99 | 6.93 | 5.66 |
| Found: | 67.83 | 6.92 | 5.60 |

Nuclear magnetic resonance spectra ($CDCl_3$; ppm):

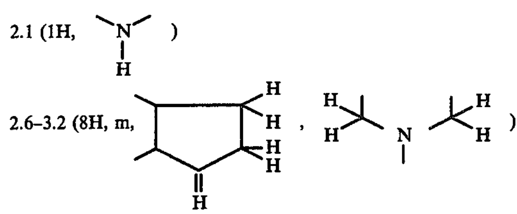

EXAMPLE 22

A mixture of 4.7 g. of a mixture of 1-(4-indenyloxy)-2,3-epoxypropane and 1-(7-indenyloxy)-2,3-epoxypropane, 11.5 g. of 2-chloroethylamine hydrochloride, 10 g. of sodium hydroxide, 100 ml. of ethanol, and 50 ml. of water was stirred for 24 hours at 60°-65° C. After cooling, the mixture was acidified with 5% hydrochloric acid and ethanol was distilled away under reduced pressure. The resulting aqueous solution was washed with ethyl acetate, alkalified with an aqueous 5% sodium hydroxide solution, and then extracted three times each time with 50 ml. of ether. The extracts were combined and dried over anhydrous sodium sulfate and then ether was distilled away from the extract under reduced pressure. The oily material obtained was subjected to a silica gel chromatography and eluted by a solvent mixture of chloroform: methanol (9 : 1) and from the eluate 500 mg. of a mixture of 2-(4-indenyloxymethyl) morpholine and 2-(7-indenyloxy methyl) morpholine (the proportions of 7-indenyl isomer : 4-indenyl isomer was 17 : 8 was obtained.

The product obtained coincided completely with the product obtained in Example 19-a).

EXAMPLE 23

Into 10.6 ml. of pyridine was added 2.5 g. of chlorosulfonic acid with stirring at 0°-5° C. and then 5.0 g. of a mixture of 1-(4-indenyloxy)-3-β-hydroxyethylamino-2-propanol and 1-(7-indenyloxy)-3-β-hydroxyethylamino-2-propanol dissolved in 10 ml. of pyridine was added dropwise to the mixture. The reaction mixture was stirred for 3 hours at 25° C. and then the solvent was distilled away under reduced pressure. The oily material obtained was added to a solution consisting of 2.4 g. of sodium hydroxide, 13 ml. of water, and 26.4 ml. of ethanol and refluxed for 24 hours.

After cooling the reaction mixture, ethanol was distilled away under reduced pressure, 50 ml. of water was added to the residue, and the mixture was extracted three times each time with 50 ml. of ether. The extracts were combined, dried over anhydrous sodium sulfate, and then ether was distilled away under reduced pressure. The residue formed was subjected to silica gel column chromatography and eluted by a solution mixture of chloroform and methanol (9 : 1). From the eluate, 1.1 g. of a mixture of 2-(4-indenyloxymethyl) morpholine and 2-(7-indenyloxymethyl) morpholine (the proportions of the 7-indenyl compound and the 4-indenyl compound was 17 : 8) was obtained. The product obtained coincided completely with that obtained in Example 19*a*.

EXAMPLES 24–30

Following the processes illustrated in Examples 19–23, the following compounds were prepared:

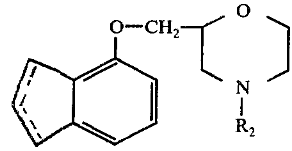

Each of the products prepared was a mixture of 4-indenyloxymethyl morpholine derivative and 7-indenyloxymethylmorpholine derivative.

EXAMPLE 24

$R^2$: $—CH_3$ Property: Elemental analysis for $C_{18}H_{19}O_2N$:

| | C(%) | H(%) | N(%) |
|---|---|---|---|
| Calculated: | 73.44 | 7.81 | 5.71 |
| Found: | 73.59 | 7.93 | 5.69 |

EXAMPLE 25

$R^2$: $—C_2H_5$ Property: Elemental analysis for $C_{16}H_{21}O_2N$:

| | C(%) | H(%) | N(%) |
|---|---|---|---|
| Calculated: | 74.10 | 8.16 | 5.40 |
| Found: | 73.83 | 7.99 | 5.41 |

EXAMPLE 26

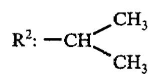

Property: Elemental analysis for $C_{17}H_{23}O_2N$:

| | C(%) | H(%) | N(%) |
|---|---|---|---|
| Calculated: | 74.69 | 8.48 | 5.12 |
| Found: | 74.41 | 8.23 | 4.98 |

EXAMPLE 27

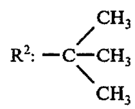

Property: Elemental analysis for $C_{18}H_{25}O_2N$:

| | C(%) | H(%) | N(%) |
|---|---|---|---|
| Calculated: | 75.23 | 8.77 | 4.87 |
| Found: | 75.39 | 8.78 | 4.90 |

EXAMPLE 28

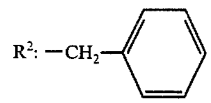

Property: Elemental analysis for $C_{21}H_{23}O_2N$:

| | C(%) | H(%) | N(%) |
|---|---|---|---|
| Calculated: | 78.47 | 7.21 | 4.36 |
| Found: | 78.11 | 7.32 | 4.59 |

EXAMPLE 29

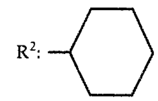

Property: Elemental analysis for $C_{20}H_{27}O_2N$:

| | C(%) | H(%) | N(%) |
|---|---|---|---|
| Calculated: | 76.64 | 8.68 | 4.47 |
| Found: | 76.73 | 8.67 | 4.53 |

EXAMPLE 30

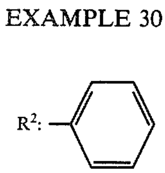

Property: Elemental analysis for $C_{20}H_{21}O_2N$:

| | C(%) | H(%) | N(%) |
|---|---|---|---|
| Calculated: | 78.15 | 6.89 | 4.56 |
| Found: | 78.33 | 6.71 | 4.44 |

EXAMPLE 31

In 20 ml. of acetone was suspended 10 g. of a mixture 3 : 7) of 2-(4-indenyloxymethyl)morpholine hydrochloride and 2-(7-indenyloxymethyl)morpholine hydrochloride and after adding to the suspension 3 g. of a mixture (3 : 7) of 2-(4-indenyloxymethyl)morpholine and 2-(7-indenyloxymethyl)-morpholine, the resultant mixture was stirred for 24 hours at room temperature. The crystals thus precipitated were recovered by filtration, thoroughly washed with acetone, and 10 g. of the crude crystals recovered were recrystallized from 40 ml. of methanol to provide 7.0 g. of 2-(7-indenyloxymethyl)-morpholine hydrochloride.

Elemental analysis for $C_{14}H_{18}O_2NCl$:

| | C(%) | H(%) | N(%) | Cl(%) |
|---|---|---|---|---|
| Calculated: | 62.80 | 6.78 | 5.23 | 13.24 |
| Found: | 63.01 | 6.75 | 5.11 | 12.98 |

Nuclear magnetic resonance spectra ($CDCl_3$ + $D_6$-DMSO):

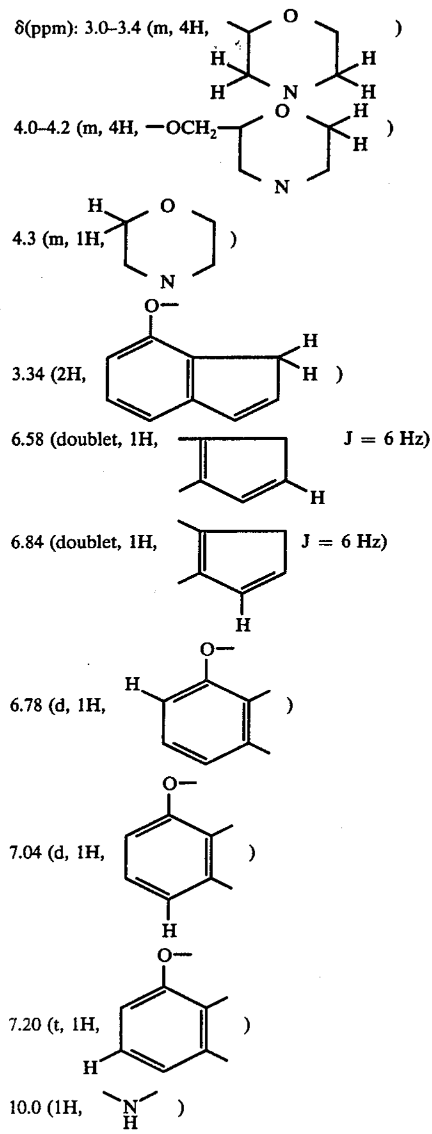

EXAMPLE 32

In 20 ml. of isopropyl alcohol was dissolved a mixture of 10 g. (0.043 mol) (3 : 7) of 2-(4-indenyloxymethyl)-morpholine and 2-(7-indenyloxymethyl)morpholine and after adding to the solution 5.9 ml. (0.032 mol) of 20% w/v hydrogen chloride in isopropyl alcohol, the mixture was stirred for 24 hours at room temperature. The crystals thus precipitated were recovered by filtration, thoroughly washed with acetone, and then recrystallized from 40 ml. of methanol to provide 7.7 g. of 2-(7-indenyloxymethyl)morpholine hydrochloride.

Elemental analysis for $C_{14}H_{18}O_2NCl$:

| | C(%) | H(%) | N(%) | Cl(%) |
|---|---|---|---|---|
| Calculated: | 62.80 | 6.78 | 5.23 | 13.24 |
| Found: | 62.54 | 6.63 | 5.08 | 13.00 |

EXAMPLE 33

In 20 ml. of methanol was suspended 10 g. of a mixture (3 : 7) of 2-(4-indenyloxymethyl)morpholine hydrochloride and 2-(7-indenyloxymethyl)morpholine hydrochloride and after adding to the suspension 0.3 g. of triethylamine, the mixture was stirred for 24 hours at room temperature. The crystals thus precipitated were recovered by filtration, thoroughly washed with acetone, and recrystallized from 40 ml. of methanol to provide 6.3 g. of 2-(7-indenyloxymethyl)-morpholine hydrochloride.

Elemental analysis for $C_{14}H_{18}O_2NCl$:

| | C(%) | H(%) | N(%) | Cl(%) |
|---|---|---|---|---|
| Calculated: | 62.80 | 6.78 | 5.23 | 13.24 |
| Found: | 62.77 | 6.83 | 5.40 | 13.29 |

EXAMPLE 34

In 500 ml. of ethanolic hydrochloric acid (350 ml. of 0.5 N hydrochloric acid and 150 ml. of ethanol) was dissolved 5.0 g. of 4-triphenylmethyl-2-(1-hydroxy-4-indanyloxymethyl)-morpholine and the solution was refluxed 17 hours. After cooling the reaction mixture, ethanol was distilled away under reduced pressure until the whole volume of the reaction mixture became about 350 ml. Sodium chloride was added to the reaction mixture to cause salting out and the mixture was extracted three times each time with 200 ml. of chloroform. The chloroform extracts were combined, dried over anhydrous magnesium sulfate, and then the solvent was distilled away under reduced pressure. Then, by adding acetone to the syrupy residue formed, 2.0 g. of 2-(7-indenyloxymethyl)morpholine hydrochloride was obtained as a precipitate.

Melting point of the hydrochloride: 155°–156° C.

Melting point of the maleate: 154°–156° C.

Elemental analysis for $C_{14}H_{18}NO_2Cl$:

| | C(%) | H(%) | N(%) | Cl(%) |
|---|---|---|---|---|
| Calculated: | 62.75 | 6.78 | 5.23 | 13.24 |
| Found: | 62.81 | 6.79 | 5.40 | 13.11 |

Nuclear magnetic resonance spectra ($CDCl_3$ + $D_6$-DMSO):

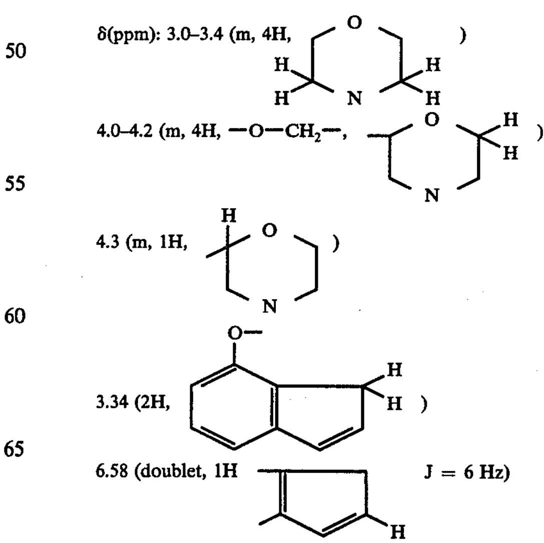

-continued 6.84 (doublet, 1H J = 6 Hz)

6.78 (d, 1H, )

7.04 (d, 1H, )

7.20 (t, 1H, )

10.0 (1H, N H )

EXAMPLE 35

By following the similar procedure as in Example 34 using 5.0 g. of 4-triphenylmethyl-2-(1-hydroxy-7-indanyloxymethyl)-morpholine, a syrupy residue was obtained and by adding to the residue isopropanol, 2.1 g. of 2-(4-indenyloxymethyl)-morpholine hydrochloride was obtained as a precipitate.

Melting point of the hydrochloride: 175°-176° C.

Melting point of the maleate: 167°-169° C.

Elemental analysis for $C_{14}H_{18}NO_2Cl$:

| | C(%) | H(%) | N(%) | Cl(%) |
|---|---|---|---|---|
| Calculated: | 62.75 | 6.78 | 5.23 | 13.24 |
| Found: | 62.90 | 6.80 | 5.31 | 13.28 |

Nuclear magnetic resonance spectra ($CDCl_3$ + $D_6$-DNSO):

δ(ppm): 3.0-3.4 (m, 4H, )

4.0-4.1 (m, 4H, —O—$CH_2$— )

4.3 (m, 1H, )

3.4 (2H, )

6.5 (doublet, 1H, J = 6 Hz)

-continued 7.0 (doublet, 1H, J = 6 Hz)

6.8 (q, 1H, )

7.1 (d, 2H, )

9.5 (1H, N H )

EXAMPLE 36

To 1.0 g. of 2-(1-hydroxy-4-indanyloxymethyl)morpholine were added 50 ml. of ethanol and 50 ml. of 0.5 N hydrochloric acid and the mixture was refluxed for 17 hours. After cooling, the reaction mixture was concentrated under reduced pressure until the whole volume became about 50 ml and then sodium chloride was added thereto to cause salting out. The reaction mixture was extracted three times each time with 50 ml. of chloroform. The extracts were combined, dried over anhydrous magnesium sulfate, and the solvent was distilled away. The syrupy residue formed was dissolved in a small amount of isopropyl alcohol and then acetone was added to the solution to provide 830 mg. of light yellow powder of 2-(7-indenyloxymethyl)morpholine hydrochloride as the precipitates.

By recrystallizing the product from acetone, the colorless acicular crystals of the aimed compound having a melting point of 155°-156° C. were obtained.

Elemental analysis for $C_{14}H_{18}NO_2Cl$:

| | C(%) | H(%) | N(%) | Cl(%) |
|---|---|---|---|---|
| Calculated: | 62.75 | 6.78 | 5.23 | 13.24 |
| Found: | 63.43 | 6.72 | 5.43 | 12.91 |

Nuclear magnetic resonance spectra ($CDCl_3$ + $D_6$—DMSO)

δ(ppm): 3.0-3.4 (m, 4H, )

4.0-4.2 (m, 4H, —$OCH_2$— )

4.3 (m, 1H, )

3.34 (2H, )

-continued

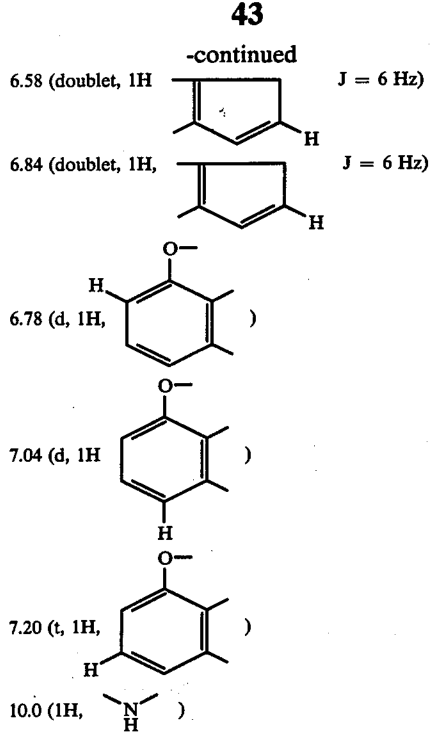

EXAMPLE 37

To 1.0 g. of 2-(1-hydroxy-7-indanyloxymethyl)morpholine were added 50 ml. of ethanol and 50 ml. of 0.5 N hydrochloric acid and the mixture was refluxed for 8 hours. Then, the reaction mixture was similarly treated as in Example 36 to provide 500 mg. of 2-(4-indenyloxymethyl)morpholine hydrochloride. The product was then recrystallized from isopropyl alcohol to provide the aimed compound having a melting point of 175°-176° C.

Elemental analysis for $C_{14}H_{18}NO_2Cl$:

| | C(%) | H(%) | N(%) | Cl(%) |
|---|---|---|---|---|
| Calculated: | 62.75 | 6.78 | 5.23 | 13.24 |
| Found: | 63.00 | 6.81 | 5.39 | 13.56 |

Nuclear magnetic resonance spectra ($CDCl_3$ + $D_6$—DMSO)

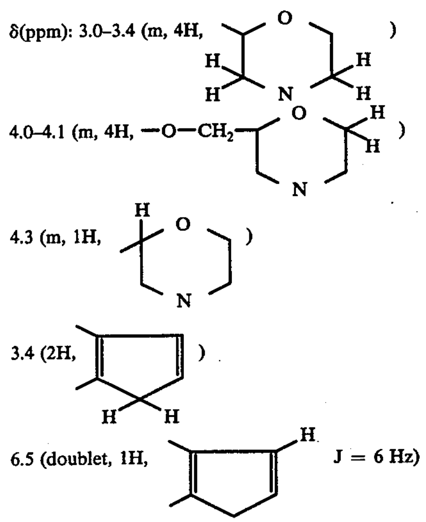

-continued

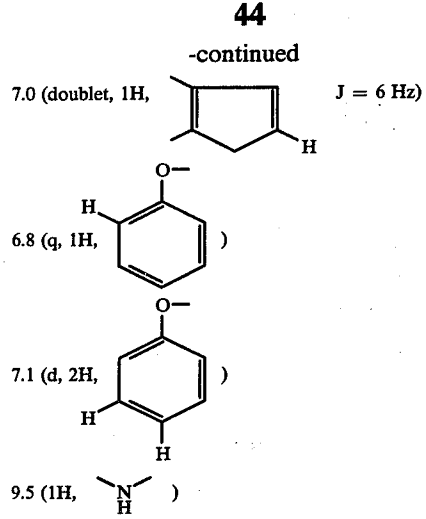

What is claimed is:

1. A 2-(indenyloxymethyl)morpholine compound of the formula:

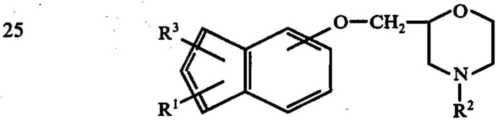

wherein $R^1$ and $R^3$ each represents a hydrogen atom, a lower alkyl group or a phenyl group, $R^2$ is a hydrogen atom, a lower alkyl group, a cycloalkyl group having 5-6 carbon atoms, a phenyl group, or a benzyl group, one of the dotted lines representing a single bond and the other is a double bond and the non-toxic pharmaceutically acceptable acid addition salts thereof including tautomeric mixtures thereof.

2. A compound as claimed in claim 1 wherein said $R^1$ and $R^3$ are both hydrogen atoms and said $R^2$ is a lower alkyl group.

3. A compound as claimed in claim 1 which is 2-(7-indenyloxymethyl)-4-isopropylmorpholine and an acid addition salt thereof.

4. A compound as claimed in claim 1 which is 4-butyl-2-(7-indenyloxymethyl)morpholine and an acid addition salt thereof.

5. A compound as claimed in claim 1 which is 2-(7-indenyloxymethyl)-4-isopropylmorpholine and an acid addition salt thereof.

6. A compound as claimed in claim 1 which is 4-ethyl-2-(7-indenyloxymethyl) morpholine and an acid addition salt thereof.

7. A compound as claimed in claim 1 which is 2-(7-indenyloxymethyl)-4-propylmorpholine and an acid addition salt thereof.

8. A tautomeric mixture as claimed in claim 1 which is a mixture of 2-(4-indenyloxymethyl)morpholine and 2-(7-indenyloxymethyl)morpholine.

9. A compound as claimed in claim 1 which is 2-(3-methyl-7-indenyloxymethyl) morpholine.

10. A compound as claimed in claim 1 which is 4isopropyl-(3-methyl-4-indenyloxymethyl) morpholine.

11. A compound as claimed in claim 1 which is 4-isopropyl-(3-methyl-7-indenyloxymethyl) morpholine.

12. A compound according to claim 1 wherein the salts are the citrate and maleate salts.

13. A compound as claimed in claim 1 which is an acid addition salt of 2-(7-indenyloxymethyl) morpholine.

* * * * *

UNITED STATES PATENT OFFICE

CERTIFICATE OF CORRECTION

Patent No. 4,109,088 Dated August 22, 1978

Inventor(s) Masuo Murakami, et al

It is certified that error appears in the above-identified patent and that said Letters Patent are hereby corrected as shown below:

Column 40, line 36: change "155°-156°C." to --168°-172°C.--.

Column 42, line 41: change "155°-156°C." to --168°-172°C.--.

Signed and Sealed this

*Twelfth* Day of *August 1980*

[SEAL]

*Attest:*

SIDNEY A. DIAMOND

*Attesting Officer* *Commissioner of Patents and Trademarks*

UNITED STATES PATENT AND TRADEMARK OFFICE

CERTIFICATE OF CORRECTION

PATENT NO. : 4,109,088

DATED : August 22, 1978

INVENTOR(S) : Murakami et al.

It is certified that error appears in the above-identified patent and that said Letters Patent is hereby corrected as shown below:

In claim 1 change the chemical formula

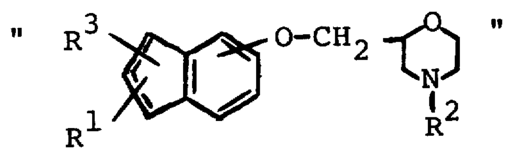

to

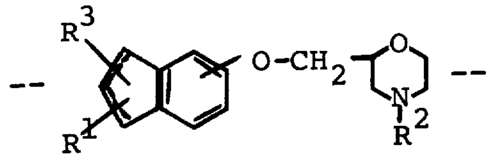

Signed and Sealed this

*Nineteenth* Day of *November 1985*

[SEAL]

*Attest:*

DONALD J. QUIGG

*Attesting Officer* *Commissioner of Patents and Trademarks*